United States Patent [19]
Yamada et al.

[11] Patent Number: 5,760,033
[45] Date of Patent: Jun. 2, 1998

[54] 1,3 OXA (THIA) ZINES AND PEST CONTROL AGENTS

[76] Inventors: Yasuo Yamada, 1864 Kouzu, Odawara, Kanagawa, 256, Japan; Takashi Kishimoto, 450-128 Ojiri, Hadano, Kanagawa, 247, Japan; Michihiko Matsuda, 5-14-12-253 Ougicho, Odawara, Kanagawa, 250, Japan; Renpei Hatano, 5-24-37-103 Ougicho, Odawara, Kanagawa, 250, Japan; Takao Iwasa, 237-5-202 Nakazato, Odawara, Kanagawa, 250, Japan; Makio Yano, 2002-1, Kando, Yoshida-cho, Haibara-gun, Shizuoka, 421-03, Japan

[21] Appl. No.: 481,338

[22] PCT Filed: Dec. 22, 1993

[86] PCT No.: PCT/JP93/01856

§ 371 Date: Aug. 25, 1995

§ 102(e) Date: Aug. 25, 1995

[87] PCT Pub. No.: WO94/14783

PCT Pub. Date: Jul. 7, 1994

[30] Foreign Application Priority Data

| Dec. 25, 1992 | [JP] | Japan | 4/359504 |
| Apr. 30, 1993 | [JP] | Japan | 5/128334 |
| Jun. 28, 1993 | [JP] | Japan | 5/181938 |
| Sep. 2, 1993 | [JP] | Japan | 5/241952 |
| Nov. 19, 1993 | [JP] | Japan | 5/314072 |

[51] Int. Cl.⁶ ............ A61K 31/54; A61K 31/535; C07D 279/06; C07D 265/06
[52] U.S. Cl. ............ 514/226.8; 514/228.8; 544/53; 544/54; 544/55; 544/88; 544/96
[58] Field of Search ............ 54/53, 54, 55, 54/88, 96; 514/226.8, 228.8

[56] References Cited

FOREIGN PATENT DOCUMENTS

| 0 635 500 | 8/1994 | European Pat. Off. . |
| 927515 | 1/1972 | Italy . |

OTHER PUBLICATIONS

Gazz.Chim.Ital., 104, 1181–1193 (1974) Giordano et al.
Gazz.Chim.Ital., 104, (11–12), 1181–1193 (1974) Giordano et al.
J. Chem.Soc., 1(8), 771–774 (1973) Abis et al.
Zh. Org. Khim., 18, 178–181 (1982) Pavel.
Chem.Ab. 86:55459, 1972, Giordano, Abstract of It 927, 515.

*Primary Examiner*—Matthew V. Grumbling

[57] ABSTRACT

A compound represented by the chemical formula [1]:

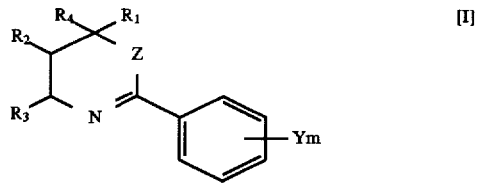

wherein Z is oxygen or sulfur, Y is halogen, optionally substituted alkyl, optionally substituted alkoxycarbonyl, optionally substituted alkoxy, $S(O)_p r^1$ wherein p denotes an integer from 0 to 2, $r^1$ is optionally substituted alkyl, nitro, cyano or optionally substituted amino, m denotes an integer from 1 to 3, $R_1$, $R_2$ and $R_4$ are same or different one another and each independently hydrogen, optionally substituted alkyl or optionally substituted phenyl, $R_3$ is alkyl, alkenyl, aralkyl, cycloalkyl, phenyl, naphthyl, pyridyl, furyl or thienyl, those which substituents can be further optionally substituted by halogen, hydroxy, optionally substituted alkyl or the like, and a chemical agent for controlling pests.

2 Claims, No Drawings

1.3 OXA (THIA) ZINES AND PEST CONTROL AGENTS

This is a 371 of PCT/JP93/01856 filed Dec. 22, 1993.

FIELD OF THE INVENTION

The present invention relates to novel heterocyclic derivatives and pest control agent.

BACKGROUND ARTS

Up till now, a number of insecticides and acaricides have been used for agricultural production, however, many of them do not satisfy enough such conditions as sufficient effectiveness on pests, no restriction in their use due to resistance problems raising against the agents, no phytotoxicity, no contamination in plant crops and less toxicity to humans, livestock and fishes. It is, therefore, intensively demanded to provide a chemical agent which can satisfy the aforementioned conditions and particularly safety requirements.

It is an object of the present invention to provide a chemical agent for controlling pests having firm effectiveness and usable to be safe.

The compounds similar to the compounds of the present invention have been disclosed as described hereinbelow, though their biological activities are not mentioned in those disclosures.

1) Zh. Org. Khim 18, 178 (1982)

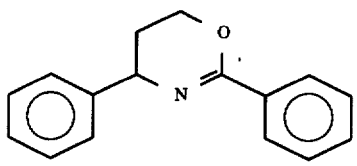

2) Gazz. Chim. Ital. 104, 1181 (1974)

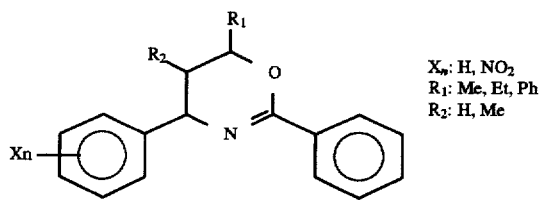

$X_n$: H, $NO_2$
$R_1$: Me, Et, Ph
$R_2$: H, Me

3) Ital. 927515 (This patent covers the above publication (2)). (CA 86.55459n) (Monomer of macromolecule)

Disclosure of the Invention

The present invention is directed to a compound represented by the general formula [I]:

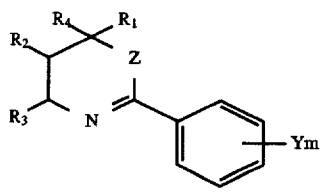

wherein Z is oxygen atom or sulfur atom; Y is a halogen atom, an optionally substituted alkyl group, an optionally substituted alkoxycarbonyl group, an optionally substituted alkoxy group, $S(O)_p$ $r^1$ wherein p denotes an integer of 0 to 2, $r^1$ denotes an optionally substituted alkyl group, nitro, cyano or an optionally substituted amino group; m is an integer of 1 to 3; $R_1$, $R_2$ and $R_4$ can be same or different one another and are each independently hydrogen atom, an optionally substituted alkyl group or an optionally substituted phenyl group; $R_3$ is an alkyl group, an alkenyl group, an aralkyl group, a cycloalkyl group, phenyl, naphthyl, pyridyl, furyl or thienyl, those which substituents can be further optionally substituted by halogen atom, hydroxy group, an optionally substituted alkyl group, an optionally substituted cycloalkyl group, an optionally substituted phenyl group, an optionally substituted alkoxy group, an optionally substituted phenoxy, an optionally substituted heterocyclic group, an optionally substituted heterocyclic-oxy group, an optionally substituted alkylthio group, an optionally substituted phenylthio group or an optionally substituted amino group, and a oest control agent.

Now, the substituents represented by Y, $R_1$, $R_2$, $R_3$ and $R_4$ are exemplified hereinbelow.

Y represents a halogen atom; a $C_1$–$C_6$ alkyl group which may be optionally substituted by halogen atom; an optionally substituted $C_1$–$C_6$ alkoxycarbonyl group; $S(O)_p$ $r^1$ wherein p denotes an integer of 0 to 2, $r^1$ represents an optionally substituted $C_1$–$C_6$ alkyl group; nitro; cyano or amino group which may be optionally substituted by mono- or di- $C_1$–$C_6$ alkyl group(s).

$R_1$, $R_2$ and $R_4$ are each independently hydrogen atom, an optionally substituted $C_1$–$C_6$ alkyl group or an optionally substituted phenyl group.

$R_3$ represents a $C_1$–$C_{18}$ alkyl group, a $C_2$–$C_6$ alkenyl group, an aralkyl, a $C_3$–$C_8$ cycloalkyl group, phenyl, naphthyl, pyridyl, furyl or thienyl, those which can be substituted by halogen atom; hydroxy group; a $C_1$–$C_{18}$ alkyl group; a $C_1$–$C_6$ alkyl group which may be optionally substituted by halogen atom, phenyl group, a halophenyl group or a $C_1$–$C_6$ alkoxyphenyl group; an optionally substituted $C_3$–$C_8$ cycloalkyl group; phenyl group which may be optionally substituted by halogen atom, a $C_1$–$C_{18}$ alkyl group, a $C_1$–$C_6$ haloalkyl group, a $C_1$–$C_6$ alkoxy group or a $C_1$–$C_6$ haloalkoxy group; a $C_1$–$C_{18}$ alkoxy group; a $C_1$–$C_6$ haloalkoxy group, a phenyl-$C_1$–$C_6$ alkoxy group which may be substituted by halogen atom, a $C_1$–$C_6$ alkyl group, a $C_1$–$C_6$ haloalkyl group, a $C_1$–$C_6$ alkoxy group or a $C_1$–$C_6$ haloalkoxy group; a pyridyl-$C_1$–$C_6$ alkoxy group which may be substituted by halogen atom; an optionally substituted $C_2$–$C_6$ alkynyloxy group; phenoxy group which may be substituted by halogen, a $C_1$–$C_6$ alkoxy group or nitro; pyridyl which may be substituted by halogen atom or a $C_1$–$C_6$ alkyl; a heterocycle-oxy group which may be substituted by halogen atom, a $C_1$–$C_6$ alkyl group, a $C_1$–$C_6$ haloalkyl group or a $C_1$–$C_6$ alkoxy group; $S(O)_q$ $r^2$ wherein q denotes an integer of 0, 1 or 2, $r^2$ represents an optionally substituted $C_1$–$C_6$ alkyl group or phenyl which may be substituted by halogen or the like; and amino group which may be substituted by mono- or di- $C_1$–$C_6$ alkyl group(s).

The compounds according to the present invention can be prepared by the following method.

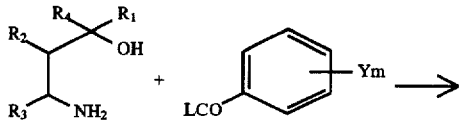

-continued

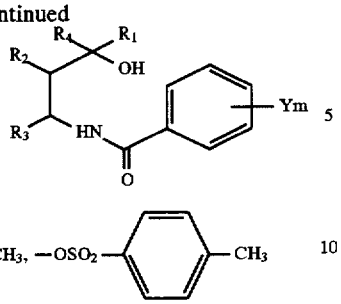

L: Halogen, —OH, —OSO₂CH₃, —OSO₂—⟨phenyl⟩—CH₃

The reaction is carried out in an inert solvent such as benzene, tetrahydrofuran, acetonitrile and N,N-dimethylformamide, at a temperature of from −20° C. to the boiling point of the solvent, for from about 30 minutes to several dozen of hours, if necessary and desired, by using either a base as triethylamine, pyridine and sodium hydroxide or using a dehydrazing agent such as consentrated sulfuric acid, dicyclohexylcarbodiimide.

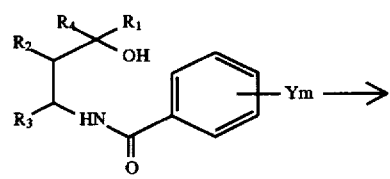

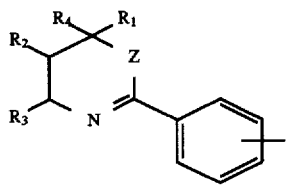

When the reaction is carried out in an inert solvent such as tetrahydrofuran and benzene at a temperature of from −20° C. to the boiling point of the solvent, for from about 30 minutes to several dozen of hours, by optionally using a dehydrating agent such as dialkyl azodicarboxylate and a deoxydating agent such as triphenylphosphine, the compound of which substituent Z is oxygene can be obtained.

When any of Lawesson's Reagent, or phosphorus pentasulfide or the like is used in the reaction, the compound of which substituent Z is sulfur can be obtained.

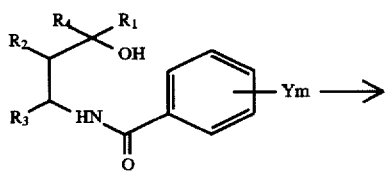

(2)

-continued

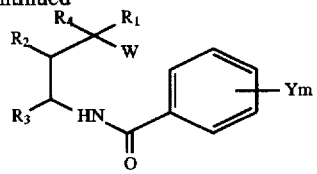

(Wherein W is halogen atom or RSO₃, wherein R represents $C_1$–$C_6$ alkyl or phenyl which may be substituted, such as p-Tolyl group)

The reaction is carried out in an inert solvent such as benzene, tetrahydrofuran and chloroform at a temperature of from −20° C. to the boiling point of the solvent, for from about 30 minutes to several dozen of hours, by using either a halogenating agent such as thionyl chloride, phosphorus oxychloride, phosphorus trichloride and phosphorus pentachloride, or R-SO₂Cl and a base such as triethyamine, pyridine, sodium hydroxide and sodium carbonate.

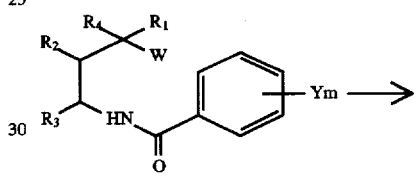

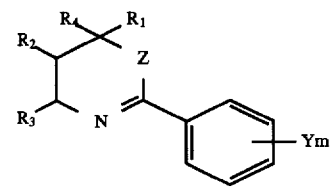

Z: O or S

The reaction is carried out in an inert solvent such as water, ethyl alcohol, tetrahydrofuran, benzene, chloroform, N,N-dimethylformamide, acetonitrile, dioxane and dichloromethane or without solvent, at a temperature of from −20° C. to the boiling point of the solvent, for from about 30 minutes to several dozen of hours, if necessary and desired, by using either a base such as sodium hydride, sodium hydroxide, sodium carbonate, triethylamine and pyridine, or a dehydrating agent such as sulfuric acid and phosphorus pentaoxide.

When any of Lawesson's Reagent, or phosphorus pentasulfide or the like is used as the dehydrating agent in the reaction, the compound of which substituent Z is sulfur atom can be obtained.

Depending upon the type of substituents, the compound of the present invention can be prepared by appropriately selecting any of the following equatin, or known or the similar reactions.

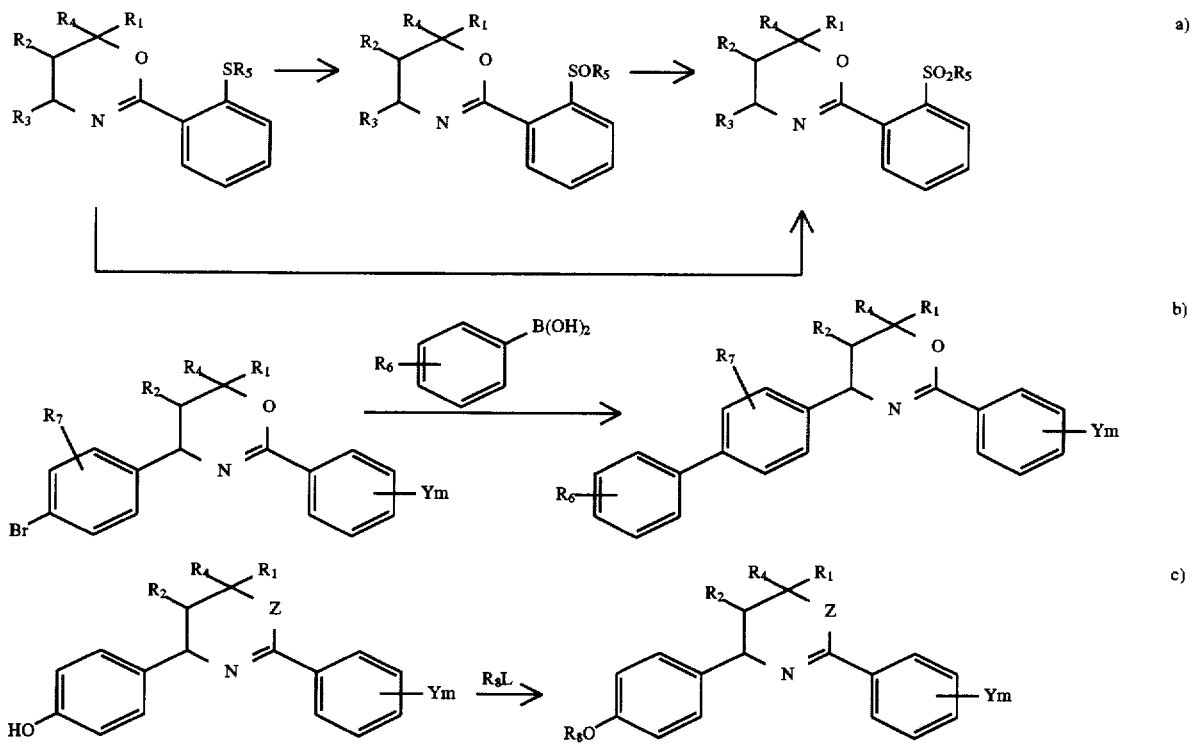

Whichever the reaction is employed, the objective compounds can be obtained according to normal post-reaction procedures.

The chemical structure of the compounds of the present invention was determined from the analytical results obtained by IR, NMR, MS, etc.

BEST MODE FOR CARRYING OUT THE INVENTION

Now, the present invention is further described in detail with referring to the examples.

Reference 1

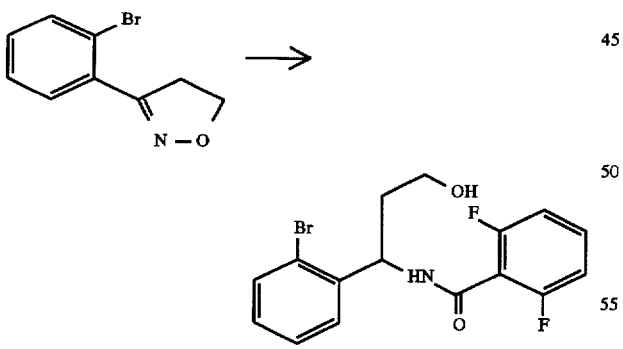

To a solution of 18.8 g of 3-(2-bromophenyl)-4,5-dihydroisooxazole in 200 ml of tetrahydrofuran at 0° C. was added 11.5 ml of boron trifluoride diethyl etherate and 11.5 ml of boran-methyl sulfide complex(10M). The reaction mixture was refluxed for 6 hours. After cooling, 90 ml of a 5N aqueous solution of sodium hydroxide was added to the solution and the reaction mixture was refluxed for 1 hour.

After cooling, the organic layer was separated and concentrated under reduced pressure. The resulting solid was recrystallized from n-haxane to afford 17.9 g of N-[1-(2-bromophenyl)-3-hydroxypropyl]-2,6-difluorobenzamide. m.p. 63°–65° C.

Reference 2

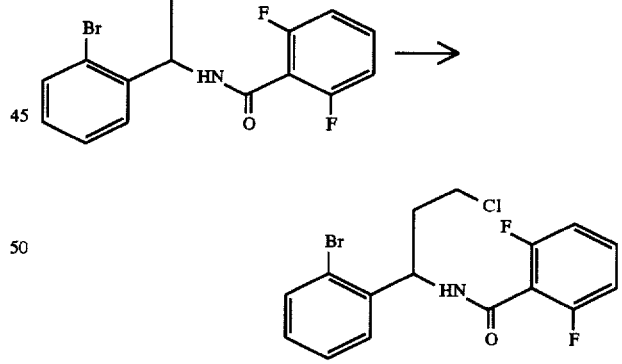

To a solution of 12.9 g of N-[1-(2-bromophenyl)-3-hydroxypropyl]-2,6-difluorobenzamide in 80 ml of benzene under refluxing, was added dropwise 5.0 g of thionyl chloride for 10 minutes and stirring continued for an additional 30 minutes. Aftercooling, the precipitated solid was filtered, washed several times with n-hexane and dried to afford 13.0 g of N-[1-(2-bromophenyl)-3-chloropropyl]-2,6-difluorobenzamide. m.p. 183°–185° C.

Example 1

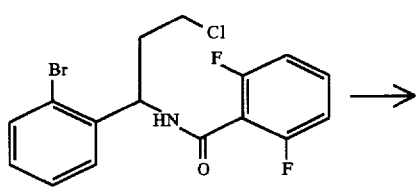

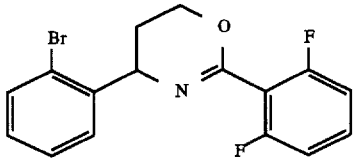

To a solution of 10.0 g of N-[1-(2-bromophenyl)-3-chloropropyl]-2,6-difluorobenzamide in 60 ml of N,N-dimethylformamide at a temperature of from 5° C. to 10° C., was added portionwise 1.1 g of 60% dispersion in mineral oil of sodium hydride. The reaction mixture was stirred at room temperature for 2 hours. The reaction mixture was poured into iced water and extracted with ethyl acetate. The ethyl acetate solution was washed with water, dried over magnesium sulfate and concentrated under reduced pressure. The residue was subjected to silica gel chromatography to afford 7.4 g of 2-(2,6-difluorophenyl)-4-(2-bromophenyl)-5,6-dihydro-4H-1,3-oxazine. $N_D^{23.0}$ 1.5750

Reference Example 3

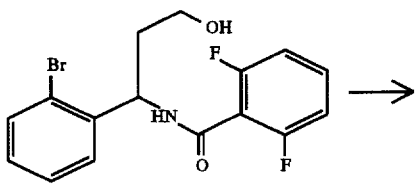

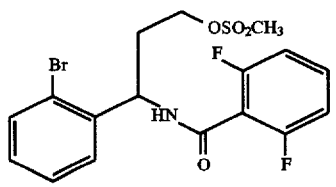

To a solution of 15.0 g of N-[1-(2-bromophenyl)-3-hydroxypropyl]-2,6-difluorobenzamide, 4.5 g of triethylamine in 150 ml of dichloromethane at room temperature, was added dropwise 5.1 g of methylsulfonyl chloride and stirring continued for an additional 30 minutes. The reaction mixture was poured into iced water and extracted with ethyl acetate. The ethyl acetate solution was washed with water, dried over magnesium sulfate and concentrated under reduced pressure to afford 18.0 g of N-[1-(2-bromophenyl)-3-(methylsulfonyloxy)propyl]-2,6-difluorobenzamide.

Example 2

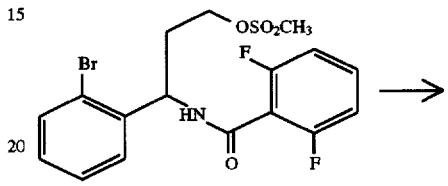

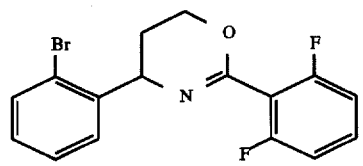

To a solution of 18.0 g of N-[1-(2-bromophenyl)-3-(methylsulfonyloxy)propyl]-2,6-difluorobenzamide in 150ml of dioxane at room temperature, was added dropwise 4.5 g of triethylamine. The reaction mixture was refluxed for 2.5 hours. After cooling, the reaction mixture was poured into iced water and extracted with ethyl acetate. The ethyl acetate solution was washed with water, dried over magnesium sulfate and concentrated under reduced pressure. The residue was subjected to silica gel chromatography to afford 12.5 g of 2-(2,6-difluorophenyl)-4-(2-bromophenyl)-5,6-dihydro-4H-1,3-oxazine.

Example 3

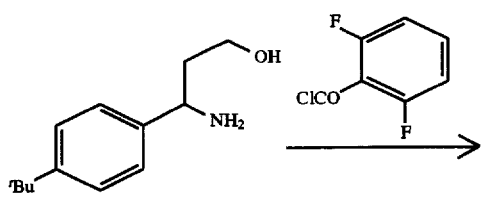

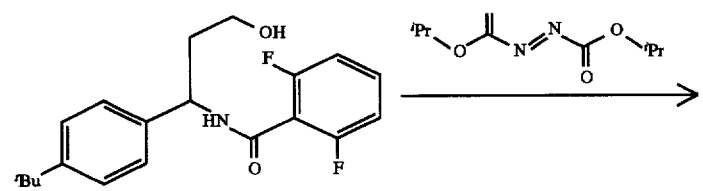

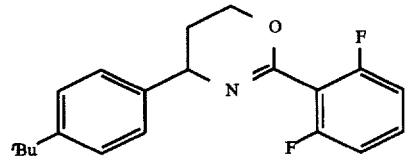

To a solution of 0.8 g of 3-(4-t-butylphenyl)-3-amino-1-propanol, 0.46 g of triethylamine in 15 ml of tetrahydrofuran at 0° C. was added dropwise 0.7 g of 2,6-difluorobenzoyl chloride. The reaction mixture was stirred at room temperature for 5 hours. The precipitared solid was filtered and the filtrate was concentrated under reduced pressure. To the residue, there was added 10 ml of tetrahydrofuran and 1.1 g of triphenylphosphine and further added 0.95 g of diisopropyl azodicarboxylate.

The reaction mixture was stirred at room temperature for 12 hours and concentrated under reduced pressure. The residue was subjected to silica gel chromatography to afford 0.4 g of 2-(2,6-difluorophenyl)-4-(4-t-butylphenyl)-5,6-dihydro-4H-1,3-oxazine as a pale yellow oil. $N_D^{22.0}$ 1.5284 ml of toluene at room temperature, was added 1.1 g of Lawesson's Reagent. The reaction mixture was refluxed for 1 hour and concentrated under reduced pressure. The residue was subjected to silica gel chromatography to afford 0.4 g of 2-(2,6-difluorophenyl)-4-(2-bromophenyl)-5,6-dihydro-4H-1,3-thiazine. m.p. 136°–138° C.

Including the compound prepared in all examples described hereinabove, the representative examples of the compounds of the present invention are illustrated in Tables 1-1 and 1-2.

EXAMPLE 4

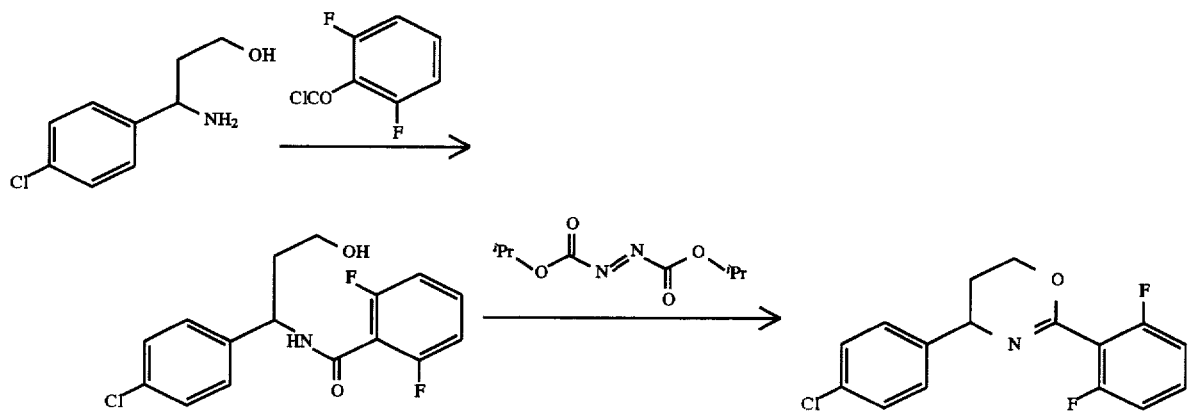

To a solution of 0.9 g of 3-(4-chlorophenyl)-3-amino-1-propanol, 0.5 g of triethylamine in 10 ml of tetrahydrofuran at 0° C., was added dropwise 0.8 g of 2,6-difluorobenzoyl chloride. The reaction mixture was stirred at room temperature for 5 hours. The precipitated solid was filtered off and the filtrate was concentrated under reduced pressure. To the residue, there was added 20 ml of tetrahydrofuran and 2.4 g of triphenylphosphine and further added 2.0 g of diisopropyl azodicarboxylate. The reaction mixture was stirred at room temperature for 12 hours and concentrated under reduced pressure. The residue was subjected to silica gel chromatography to afford 0.5 g of 2-(2,6-difluorophenyl)-4-(4-chlorophenyl)-5,6-dihydro-4H-1,3-oxazine. $N_D^{23.2}$ 1.5532

Example 5

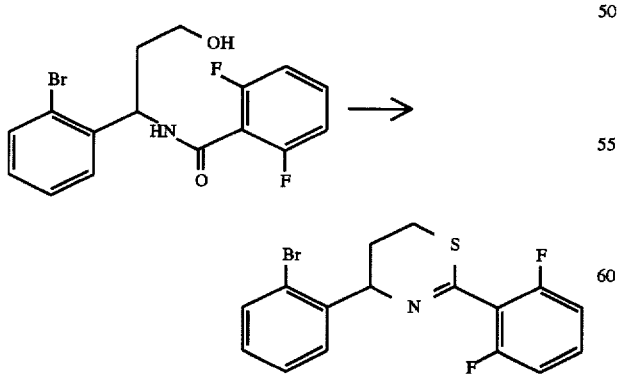

To a solution of 1.0 g of N-[1-(2-bromophenyl)-3-(methylsulfonyloxy) propyl]-2,6-difluorobenzamide in 15

TABLE 1-1

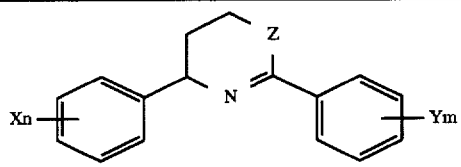

| Compound No. | Xn | Z | —Ym | Physical constant |
|---|---|---|---|---|
| I-1 | H | O | 2,6-F$_2$ | $N_D^{20.7}$ 1.5502 |
| I-2 | 4-Cl | " | " | $N_D^{23.2}$ 1.5532 |
| I-3 | 4-$^t$Bu | " | " | $N_D^{22.9}$ 1.5284 |
| I-4 | 4-OCH$_3$ | " | " | |
| I-5 | 4-O$^i$Pr | " | " | $N_D^{22.2}$ 1.5377 |
| I-6 | 4-O$^n$Oct | " | " | $N_D^{23.8}$ 1.5273 |
| I-7 | 2-Cl | " | " | $N_D^{20.7}$ 1.5500 |
| I-8 | 3-Cl | " | " | $N_D^{19.9}$ 1.5612 |
| I-9 | 2,6-Cl$_2$ | " | " | $N_D^{23.7}$ 1.5573 |
| I-10 | 2,4-Cl$_2$ | " | " | mp. [109–111° C.] |
| I-11 | 2,4,5-Cl$_3$ | " | " | |
| I-12 | H | O | 2-Cl, 6-F | $N_D^{20.6}$ 1.5572 |
| I-13 | 4-Cl | " | " | $N_D^{23.4}$ 1.5716 |
| I-14 | 4-$^t$Bu | " | " | $N_D^{23.6}$ 1.5474 |
| I-15 | 4-OCH$_3$ | " | " | |
| I-16 | 4-O$^i$Pr | " | " | |
| I-17 | 4-O$^n$Oct | " | " | |
| I-18 | 2-Cl | " | " | $N_D^{23.8}$ 1.5710 |
| I-19 | 3-Cl | " | " | $N_D^{20.0}$ 1.5762 |
| I-20 | 2,6-Cl$_2$ | " | " | |
| I-21 | 2,4-Cl$_2$ | " | " | |
| I-22 | 2,4,5-Cl$_3$ | " | " | |
| I-23 | 4-F | O | 2,6-F$_2$ | $N_D^{22.9}$ 1.5255 |
| I-24 | 2-F | " | " | $N_D^{22.8}$ 1.5358 |
| I-25 | 4-$^n$Pr | " | " | $N_D^{23.5}$ 1.5326 |
| I-26 | 4-OCF$_3$ | " | " | $N_D^{23.3}$ 1.4939 |
| I-27 | 4-CF$_3$ | " | " | $N_D^{23.4}$ 1.5123 |
| I-28 | 2-CF$_3$ | " | " | $N_D^{23.0}$ 1.5145 |
| I-29 | 2,4-F$_2$ | " | " | $N_D^{22.8}$ 1.5191 |
| I-30 | 2-Cl, 4-F | " | " | $N_D^{23.3}$ 1.5372 |
| I-31 | 2-Cl, 6-F | " | " | $N_D^{23.8}$ 1.5358 |
| I-32 | 2-OEt, 5-Br | " | " | $N_D^{21.9}$ 1.5624 |
| I-33 | 2-Cl, 4-O$^i$Pr | " | " | $N_D^{22.7}$ 1.5257 |
| I-34 | 4-CF$_3$ | " | 2-Cl, 6-F | $N_D^{23.4}$ 1.5179 |
| I-35 | 2-Cl, 6-F | " | " | $N_D^{23.8}$ 1.5462 |
| I-36 | H | " | 2,6-Cl$_2$ | $N_D^{20.6}$ 1.5767 |
| I-37 | 4-Cl | " | " | $N_D^{23.6}$ 1.5815 |
| I-38 | 3-Cl | O | 2,6-Cl$_2$ | $N_D^{19.9}$ 1.5798 |
| I-39 | 2-Cl | " | " | $N_D^{23.9}$ 1.5854 |
| I-40 | 4-$^t$Bu | " | " | amorphous* |
| I-41 | 4-CF$_3$ | " | " | $N_D^{23.7}$ 1.5371 |
| I-42 | 2-Cl | " | 2-Cl | $N_D^{23.8}$ 1.5845 |
| I-43 | 2-Br | " | 2,6-F$_2$ | $N_D^{23.0}$ 1.5750 |
| I-44 | 4-Br | " | " | $N_D^{21.2}$ 1.5737 |
| I-45 | 3-OPh | " | " | $N_D^{23.8}$ 1.5702 |
| I-46 | 4-OPh | " | " | $N_D^{22.5}$ 1.5772 |
| I-47 | 2-OPh | " | " | |
| I-48 | 4-NMe$_2$ | " | " | |
| I-49 | 4-SPh | " | " | |
| I-50 | 2-S—⟨C$_6$H$_4$⟩—Cl | " | " | |
| I-51 | 2,3-Cl$_2$ | " | " | mp. [62–65° C.] |
| I-52 | 3,4-Cl$_2$ | " | " | $N_D^{23.5}$ 1.5612 |
| I-53 | 3,5-Cl$_2$ | O | 2,6-F$_2$ | |
| I-54 | 2,5-Cl$_2$ | " | " | |
| I-55 | 2,6-F$_2$ | " | " | mp. [82–84° C.] |
| I-56 | 2-F, 4-Cl | " | " | mp. [107–110° C.] |
| I-57 | 2-Cl, 4-Br | " | " | |
| I-58 | 2-Br, 4-F | " | " | |
| I-59 | 2-Br, 6-F | " | " | |
| I-60 | 2-Br, 4-Cl | " | " | |
| I-61 | 2-Cl, 3-F | " | " | |
| I-62 | 2-Cl, 3-Br | " | " | |
| I-63 | 2-Cl, 3-CH$_3$ | " | " | |

TABLE 1-1-continued

| Compound No. | Xn | Z | −Ym | Physical constant |
|---|---|---|---|---|
| I-64 | 2-Cl, 3-OEt | " | " | |
| I-65 | 2-Cl, 3-CH$_3$ | " | " | |
| I-66 | 2-Cl, 3-OPh | " | " | |
| I-67 | 2-Cl, 3-$^t$Bu | " | " | |
| I-68 | 2-F, 3-Cl | O | 2,6-F$_2$ | |
| I-69 | 2-Br, 3-Cl | " | " | |
| I-70 | 3-Br, 4-Cl | " | " | Vis. oil* |
| I-71 | 2-Cl, 4-CF$_3$ | " | " | |
| I-72 | 2-Cl, 4-$^t$Bu | " | " | |
| I-73 | 2-Cl, 4-OCH$_2$CF$_3$ | " | " | |
| I-74 | 2-Br, 4-OEt | " | " | |
| I-75 | 2-F, 4-$^t$Bu | " | " | |
| I-76 | 2,4-(CH$_3$)$_2$ | " | " | mp. [104–106° C.] |
| I-77 | 2,3-(CH$_3$)$_2$ | " | " | |
| I-78 | 3-Br, 4-OEt | " | " | |
| I-79 | 2-OEt, 4-Cl | " | " | $N_D^{21.1}$ 1.5463 |
| I-80 | 2-OEt, 4-$^t$Bu | " | " | mp. [130–132° C.] |
| I-81 | 2-OEt, 5-Cl | " | " | |
| I-82 | 2-OEt, 5-Br | " | " | |
| I-83 | 2-O$^n$Pr, 5-Br | O | 2,6-F$_2$ | |
| I-84 | 3,4-(OEt)$_2$ | " | " | $N_D^{23.7}$ 1.5331 |
| I-85 | 3-OEt, 4-$^t$Bu | " | " | |
| I-86 | 3-$^t$Bu, 4-OEt | " | " | Vis. oil* |
| I-87 | 3-$^t$Bu, 4-O$^n$Pr | " | " | $N_D^{21.5}$ 1.5277 |
| I-88 | 4-O-(3-Cl, 5-CF$_3$-pyridin-2-yl) | " | " | Vis. oil* |
| I-89 | 4-Ph | " | " | mp. [82–85° C.] |
| I-90 | 4-OCH$_2$Ph | " | " | $N_D^{24.5}$ 1.5822 |
| I-91 | 2,3-Cl$_2$, 4-SCH$_3$ | " | " | |
| I-92 | 2,3-Cl$_2$, 4-OEt | " | " | |
| I-93 | 2,3,4-Cl$_3$ | " | " | mp. [124–126° C.] |
| I-94 | 2-OEt, 4,5-Cl$_2$ | " | " | |
| I-95 | 2-O$^n$Pen, 4,5-Cl$_2$ | " | " | |
| I-96 | 2,4-Cl$_2$, 5-Br | " | " | |
| I-97 | 2-OCH$_3$, 4-Cl, 5-Br | O | 2,6-F$_2$ | |
| I-98 | 2-OEt, 4-Cl, 5-Br | " | " | |
| I-99 | 2-O$^n$Pr, 4-Cl, 5-Br | " | " | |
| I-100 | 2-O$^n$Pen, 4-Cl, 5-Br | " | " | |
| I-101 | 2,5-(OCH$_3$)$_2$, 4-$^t$Bu | " | " | |
| I-102 | 2,5-Cl$_2$, 4-OEt | " | " | |
| I-103 | 2,3,4,5,6-F$_5$ | " | " | mp. [97–99° C.] |
| I-104 | 2,3-Cl$_2$ | " | 2-Cl, 6-F | |
| I-105 | 2,6-F$_2$ | " | " | $N_D^{22.7}$ 1.5465 |
| I-106 | 4-Br | " | " | |
| I-107 | 2-Br | " | " | |
| I-108 | 2,3,4-Cl$_3$ | " | " | |
| I-109 | 2-OEt, 3,4-Cl$_2$ | " | " | |
| I-110 | 2-O$^n$Pen, 4,5-Cl$_2$ | " | " | |
| I-111 | 2-OEt, 4-Cl, 5-Br | " | " | |
| I-112 | 2-O$^n$Pen, 4-Cl, 5-Br | O | 2-Cl, 6-F | |
| I-113 | 4-O$^i$Pr | " | 2,6-Cl$_2$ | |
| I-114 | 4-O$^n$Oct | " | " | |
| I-115 | 2,3-Cl$_2$ | " | " | |
| I-116 | 2,4-Cl$_2$ | " | " | |
| I-117 | 2-O$^n$Pr, 4-Cl, 5-Br | " | " | |
| I-118 | 4-Cl | " | 2-Cl | $N_D^{22.6}$ 1.5791 |
| I-119 | " | " | 2-F | $N_D^{22.5}$ 1.5794 |
| I-120 | " | " | 2-CF$_3$ | $N_D^{22.3}$ 1.5344 |
| I-121 | " | " | 2-CO$_2$CH$_3$ | mp. [95–98° C.] |
| I-122 | 2-Br, 5-OMe | " | 2,6-F$_2$ | Vis. oil* |
| I-123 | 2,3-Cl$_2$, 4-O$^n$Pr | " | " | mp. [89–91° C.] |
| I-124 | 3-OCH$_2$Ph | " | " | $N_D^{24.0}$ 1.5762 |

TABLE 1-1-continued
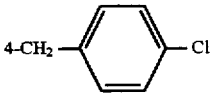
| Compound No. | Xn | Z | —Ym | Physical constant |
|---|---|---|---|---|
| I-125 | 3,5-Cl₃ | " | " | mp. [85–87° C.] |
| I-126 | 2,3-Me₂, 4-OMe | " | 2-Cl | |
| I-127 | 2-Br | O | 2-Cl | $N_D^{24.0}$ 1.6132 |
| I-128 | 2-Cl | " | 2-Br | $N_D^{23.8}$ 1.6012 |
| I-129 | 2-Br | " | " | $N_D^{23.8}$ 1.6180 |
| I-130 | 4-ⁿPen | " | 2,6-F₂ | |
| I-131 | 4-ⁿHex | " | " | |
| I-132 | 4-ⁿHep | " | " | |
| I-133 | 4-ⁿOct | " | " | |
| I-134 | 4-ⁿNon | " | " | |
| I-135 | 4-ⁿDec | " | " | |
| I-136 | 4-ⁿDodec | " | " | |
| I-137 | 4-ⁿTridec | " | " | |
| I-138 | 2-F, 4-ⁿOct | " | " | |
| I-139 | 2-Cl, 4-ⁿOct | " | " | |
| I-140 | 2-CH₃, 4-ⁿOct | " | " | |
| I-141 | 2-OCH₃, 4-ⁿOct | " | " | |
| I-142 | 2-Cl, 4-ⁿHep | O | 2,6-F₂ | |
| I-143 | 2-Cl, 4-ⁿNon | " | " | |
| I-144 | 4-cyclo Hex | " | " | |
| I-145 | 4-CH₂Ph | " | " | $N_D^{27.0}$ 1.5698 |
| I-146 | 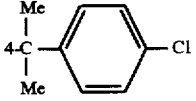 | " | " | |
| I-147 | 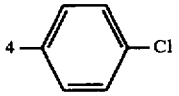 | " | " | |
| I-148 | 4-C₂H₄Ph | " | " | |
| I-149 |  | " | " | mp. [147–149° C.] |
| I-150 | 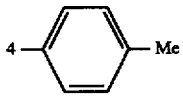 | " | " | mp. [138–140° C.] |
| I-151 | 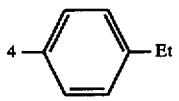 | " | " | mp. [108–111° C.] |
| I-152 |  | " | " | mp. [131–133° C.] |
| I-153 |  | " | " | mp. [106–107° C.] |
| I-154 |  | " | " | mp. [89–91° C.] |

TABLE 1-1-continued

[Structure: Xn-phenyl-CH(CH2CH2-)-N=C(Z)-phenyl-Ym]

| Compound No. | Xn | Z | —Ym | Physical constant |
|---|---|---|---|---|
| I-155 | 4-(4-tBu-phenyl) | " | " | Vis. oil* |
| I-156 | 4-(4-nHep-phenyl) | O | 2,6-F$_2$ | $N_D^{25.0}$ 1.5693 |
| I-157 | 4-(4-OMe-phenyl) | " | " | |
| I-158 | 4-(4-OnPr-phenyl) | " | " | |
| I-159 | 4-(4-OCF$_3$-phenyl) | " | " | |
| I-160 | 4-(3-Cl,4-Cl-phenyl) | " | " | Vis. oil* |
| I-161 | 4-(3-F,4-F-phenyl) | " | " | mp. [106–108° C.] |
| I-162 | 4-(3-EtO,4-Cl-phenyl) | " | " | |
| I-163 | 4-(3-Cl-phenyl) | " | " | |
| I-164 | 4-(2-Cl-phenyl) | " | " | |
| I-165 | 2-Cl, 4-(4-Cl-phenyl) | " | " | Vis. oil* |

TABLE 1-1-continued

| Compound No. | Xn | Z | −Ym | Physical constant |
|---|---|---|---|---|
| I-166 | 2-OMe, 4-(4-Cl-phenyl) | O | 2,6-F$_2$ | |
| I-167 | 2-OEt, 4-(4-Cl-phenyl) | " | " | |
| I-168 | 2-F, 4-(4-nPr-phenyl) | " | " | |
| I-169 | 2-Cl, 4-(4-nPr-phenyl) | " | " | $N_D^{26.5}$ 1.5700 |
| I-170 | 2-OMe, 4-(4-nPr-phenyl) | " | " | |
| I-171 | 2-Cl, 4-(2-Cl, 4-Cl-phenyl) | " | " | |
| I-172 | 2-F, 4-(2-Cl, 4-Cl-phenyl) | " | " | |
| I-173 | 4-(2-pyridyl) | " | " | |
| I-174 | 4-(3-pyridyl) | " | " | |
| I-175 | 4-(4-pyridyl) | " | " | |
| I-176 | 4-(2-Cl-pyridyl) | O | 2,6-F$_2$ | |
| I-177 | 4-(2-Me-pyridyl) | " | " | |

TABLE 1-1-continued

Structure: Xn-phenyl-CH(CH2CH2-)-N=C(Z)-phenyl-Ym

| Compound No. | Xn | Z | —Ym | Physical constant |
|---|---|---|---|---|
| I-178 | 4-(5-Cl-pyridin-2-yl) | " | " | |
| I-179 | 4-(5-Me-pyridin-2-yl) | " | " | |
| I-180 | 4-O-(4-Cl-phenyl) | " | " | mp. [70–74° C.] |
| I-181 | 4-O-(4-Br-phenyl) | " | " | mp. [81–83° C.] |
| I-182 | 4-S-(4-Cl-phenyl) | " | " | Vis. oil* |
| I-183 | 4-O-(pyridin-2-yl) | " | " | |
| I-184 | 4-O-(pyridin-3-yl) | " | " | |
| I-185 | 4-O-(pyridin-4-yl) | O | 2,6-F$_2$ | |
| I-186 | 4-O-(3-CF$_3$-5-Cl-pyridin-2-yl) | " | " | |
| I-187 | 3,5-Cl$_2$, 4-O-(3-CF$_3$-5-Cl-pyridin-2-yl) | " | " | |
| I-188 | 2,3-F$_2$, 4-O-(3-CF$_3$-5-Cl-pyridin-2-yl) | " | " | |

TABLE 1-1-continued

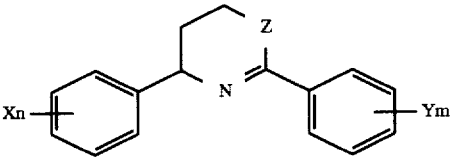

| Compound No. | Xn | Z | —Ym | Physical constant |
|---|---|---|---|---|
| I-189 | 4-OCH$_2$—⟨Ph⟩—Cl | " | " | mp. [148–150° C.] |
| I-190 | 4-OCH$_2$—⟨Ph⟩—Br | " | " | |
| I-191 | 4-OCH$_2$—⟨Ph⟩—Et | " | " | |
| I-192 | 4-OCH$_2$—⟨Ph⟩—$^t$Bu | " | " | |
| I-193 | 4-OCH$_2$—⟨Ph, 2-Cl⟩—Cl | " | " | mp. [96–98° C.] |
| I-194 | 4-OCH$_2$—⟨Ph, 2-Cl⟩—Cl | O | 2,6-F$_2$ | |
| I-195 | 2-Cl, 4-OCH$_2$—⟨Ph⟩—Cl | " | " | |
| I-196 | 2,3-Cl$_2$, 4-OCH$_2$—⟨Ph⟩—Cl | " | " | |
| I-197 | 2-Me, 4-OCH$_2$—⟨Ph⟩—Cl | " | " | |
| I-198 | 4—⟨Ph⟩—$^n$Bu | " | " | mp. [46–49° C.] |
| I-199 | 2-O$^n$Pr, 4-Cl, 5-Br | " | " | |
| I-200 | 2-O$^i$Bu, 4-Cl, 5-Br | " | " | |
| I-201 | 2-O$^n$Pen, 4-Cl, 5-Br | " | " | |
| I-202 | 2-O$^n$Pr, 4-F, 5-Br | O | 2,6-F$_2$ | |
| I-203 | 2-Cl | " | 2,6-Me$_2$ | |
| I-204 | " | " | 2,6-($^i$Pr)$_2$ | |
| I-205 | " | " | 2,6-(OMe)$_2$ | |
| I-206 | " | " | 2-NO$_2$ | |

TABLE 1-1-continued

| Compound No. | Xn | Z | —Ym | Physical constant |
|---|---|---|---|---|
| I-207 | " | " | 2-NMe₂ | |
| I-208 | " | " | 2-SMe | |
| I-209 | " | " | 2-SOMe | |
| I-210 | " | " | 2-SO₂Me | |
| I-211 | " | " | 2-CN | |
| I-212 | " | " | 2-OMe | |
| I-213 | " | " | 2,4-Cl₂ | |
| I-214 | " | " | 3,5-Cl₂ | |
| I-215 | " | " | 4-Cl | |
| I-216 | 2-Cl | O | 3-Cl | |
| I-217 | " | " | 2-I | |
| I-218 | " | S | 2-Cl | |
| I-219 | " | " | 2,6-F₂ | mp. [119–120° C.] |
| I-220 | 4—⌬ | O | 2-Cl, 6-F | |
| I-221 | 4—⌬—Cl | " | " | |
| I-222 | 4—⌬—Br | " | " | |
| I-223 | 4—⌬—Me | " | " | |
| I-224 | 4—⌬—Et | " | " | |
| I-225 | 4—⌬—ⁿPr | " | " | |
| I-226 | 4—⌬—ⁱPr | " | " | |
| I-227 | 4—⌬—ᵗBu | " | " | |
| I-228 | 4—⌬—ⁿHep | " | " | |
| I-229 | 4—⌬—OMe | " | " | |

TABLE 1-1-continued

| Compound No. | Xn | Z | —Ym | Physical constant |
|---|---|---|---|---|
| I-230 | 4—C6H4—O"Pr | " | " | |
| I-231 | 4—C6H4—OCF3 | O | 2-Cl, 6-F | |
| I-232 | 4—C6H3(2-Cl)—Cl | " | " | |
| I-233 | 4—C6H3(2-F)—F | " | " | |
| I-234 | 4—C6H3(2-OEt)—Cl | " | " | |
| I-235 | 4—C6H4—Cl (3-Cl) | " | " | |
| I-236 | 4—C6H4—Cl (2-Cl) | " | " | |
| I-237 | 2-Cl, 4—C6H4—Cl | " | " | |
| I-238 | 2-OMe, 4—C6H4—Cl | " | " | |
| I-239 | 2-OEt, 4—C6H4—Cl | " | " | |
| I-240 | 2-F, 4—C6H4—"Pr | " | " | |

TABLE 1-1-continued

[Structure: Xn-phenyl-CH(CH2CH2-Z)-N=C(-phenyl-Ym)]

| Compound No. | Xn | Z | −Ym | Physical constant |
|---|---|---|---|---|
| I-241 | 2-Cl, 4-nPr | O | 2-Cl, 6-F | |
| I-242 | 2-OMe, 4-nPr | " | " | |
| I-243 | 2-Cl, 4-(3-Cl) [2,4-Cl2] | " | " | |
| I-244 | 2-F, 4-(3-Cl) [2-F, 4-Cl with 3-Cl] | " | " | |
| I-245 | 4-(phenyl) | " | 2,6-Cl2 | |
| I-246 | 4-Cl | " | " | |
| I-247 | 4-Br | " | " | |
| I-248 | 4-Me | " | " | |
| I-249 | 4-Et | " | " | |
| I-250 | 4-nPr | " | " | |
| I-251 | 4-iPr | " | " | |
| I-252 | 4-tBu | " | " | |

TABLE 1-1-continued

| Compound No. | Xn | Z | —Ym | Physical constant |
|---|---|---|---|---|
| I-253 | 4-[phenyl]-nHep | " | " | |
| I-254 | 4-[phenyl]-OMe | O | 2,6-Cl₂ | |
| I-255 | 4-[phenyl]-OnPr | " | " | |
| I-256 | 4-[phenyl]-OCF₃ | " | " | |
| I-257 | 4-[phenyl](2-Cl, 4-Cl) | " | " | |
| I-258 | 4-[phenyl](2-F, 4-F) | " | " | |
| I-259 | 4-[phenyl](2-EtO, 4-Cl) | " | " | |
| I-260 | 4-[phenyl](3-Cl) | " | " | |
| I-261 | 4-[phenyl](2-Cl) | " | " | |
| I-262 | 2-Cl, 4-[phenyl]-Cl | " | " | |
| I-263 | 2-OMe, 4-[phenyl]-Cl | " | " | |

TABLE 1-1-continued

| Compound No. | Xn | Z | —Ym | Physical constant |
|---|---|---|---|---|
| I-264 | 2-OEt, 4-C6H4-Cl | O | 2,6-Cl2 | |
| I-265 | 2-F, 4-C6H4-nPr | " | " | |
| I-266 | 2-Cl, 4-C6H4-nPr | " | " | |
| I-267 | 2-OMe, 4-C6H4-nPr | " | " | |
| I-268 | 2-Cl, 4-C6H3(Cl)-Cl | " | " | |
| I-269 | 2-F, 4-C6H3(Cl)-Cl | " | " | |
| I-270 | 4-C6H4 | " | 2-Cl | |
| I-271 | 4-C6H4-Cl | " | " | |
| I-272 | 4-C6H4-Br | " | " | |
| I-273 | 4-C6H4-Me | " | " | |
| I-274 | 4-C6H4-Et | " | " | |
| I-275 | 4-C6H4-nPr | " | " | |

TABLE 1-1-continued

[Structure: Xn-phenyl-CH(CH2CH2-C(=Z)-phenyl-Ym)-N=]

| Compound No. | Xn | Z | −Ym | Physical constant |
|---|---|---|---|---|
| I-276 | 4-(4-iPr-phenyl) | " | " | |
| I-277 | 4-(4-tBu-phenyl) | O | 2-Cl | |
| I-278 | 4-(4-nHep-phenyl) | " | " | |
| I-279 | 4-(4-OMe-phenyl) | " | " | |
| I-280 | 4-(4-OnPr-phenyl) | " | " | |
| I-281 | 4-(4-OCF3-phenyl) | " | " | |
| I-282 | 4-(2-Cl,4-Cl-phenyl) | " | " | |
| I-283 | 4-(2-F,4-F-phenyl) | " | " | |
| I-284 | 4-(2-EtO,4-Cl-phenyl) | " | " | |
| I-285 | 4-(3-Cl-phenyl) | " | " | |
| I-286 | 4-(2-Cl-phenyl) | " | " | |

TABLE 1-1-continued

| Compound No. | Xn | Z | —Ym | Physical constant |
|---|---|---|---|---|
| I-287 | 2-Cl, 4-(C6H4)-Cl | O | 2-Cl | |
| I-288 | 2-OMe, 4-(C6H4)-Cl | " | " | |
| I-289 | 2-OEt, 4-(C6H4)-Cl | " | " | |
| I-290 | 2-F, 4-(C6H4)-nPr | " | " | |
| I-291 | 2-Cl, 4-(C6H4)-nPr | " | " | |
| I-292 | 2-OMe, 4-(C6H4)-nPr | " | " | |
| I-293 | 2-Cl, 4-(3-Cl-C6H3)-Cl | " | " | |
| I-294 | 2-F, 4-(3-Cl-C6H3)-Cl | " | " | |
| I-295 | 4-OH | " | 2,6-F₂ | 150° C. dec. |
| I-296 | 4-O-(C6H4)-NO₂ | " | " | Vis. oil* |
| I-297 | 2-OEt, 4-tBu, 5-Cl | " | " | mp. [101–103° C.] |
| I-298 | 2,3-Me₂, 4-OMe | " | " | mp. [71–73° C.] |
| I-299 | 4-CH₂-(C6H4)-OMe | " | " | |
| I-300 | 4-(C6H4)-F | " | " | mp. [134–136° C.] |

TABLE 1-1-continued
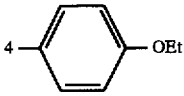
| Compound No. | Xn | Z | —Ym | Physical constant |
|---|---|---|---|---|
| I-301 | 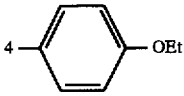 4- ◯-OEt | O | 2-Cl, 6-F | Vis. oil* |
| I-302 | " | " | 2,6-Cl$_2$ | mp. [118–120° C.] |
| I-303 | " | " | 2,6-F$_2$ | mp. [111–113° C.] |
| I-304 | 2-Cl, 4-Ph | " | " | Vis. oil* |
| I-305 | 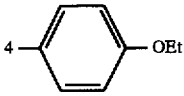 2-Cl, 4- ◯-Br | " | " | Vis. oil* |
| I-306 | 3-Cl, 4-Ph | " | " | Vis. oil* |
| I-307 | 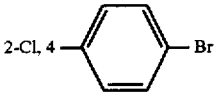 4- ◯-CF$_3$ | " | " | $N_D^{23.4}$ 1.5484 |
| I-308 | 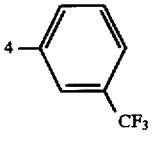 4- ◯(-Cl)-CF$_3$ | " | " | Vis. oil* |
| I-309 | 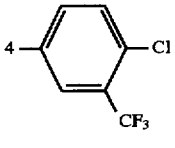 4- ◯-CF$_3$ | " | " | mp. [123–125° C.] |
| I-310 | 4-SPh | " | " | |
| I-311 | 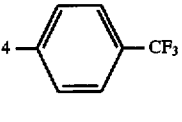 4-O- ◯-OMe | " | " | |
| I-312 | 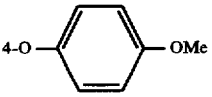 4-OCH$_2$- ◯-Me | " | " | mp. [147–149° C.] |
| I-313 | 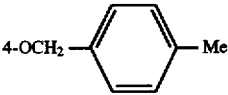 4-OCH$_2$- ◯-OMe | " | " | |
| I-314 | 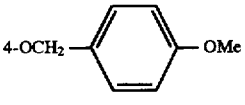 4-OCH$_2$- ◯-OCF$_3$ | " | " | |
| I-315 | 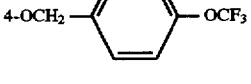 4-OCH$_2$- ◯(-Cl) | O | 2,6-F$_2$ | $N_D^{30.0}$ 1.5881 |

TABLE 1-1-continued

| Compound No. | Xn | Z | —Ym | Physical constant |
|---|---|---|---|---|
| I-316 | 4-OCH$_2$-(2-F-phenyl) | " | " | $N_D^{30.0}$ 1.5649 |
| I-317 | 4-OCH$_2$-(2-Cl-pyridin-5-yl) | " | " | $N_D^{25.0}$ 1.5765 |
| I-318 | 2,3-Cl$_2$, 4-OEt | " | " | |
| I-319 | 2,3-Cl$_2$, 4-O$^n$Pr | " | " | mp. [89–91° C.] |
| I-320 | 2-Cl, 4-$^t$Bu | " | " | |
| I-321 | 2-OMe, 4-$^t$Bu | " | " | |
| I-322 | 4-O$^t$Bu | " | " | $N_D^{25.0}$ 1.5408 |
| I-323 | 2-Br | " | 2,6-Me$_2$ | mp. [101–102° C.] |
| I-324 | " | " | 2,6-$^i$Pr$_2$ | |
| I-325 | " | " | 2,6-(OMe)$_2$ | $N_D^{24.8}$ 1.5720 |
| I-326 | " | " | 2-NO$_2$ | $N_D^{25.7}$ 1.5643 |
| I-327 | " | " | 2-NMe$_2$ | |
| I-328 | " | " | 2-SMe | $N_D^{26.7}$ 1.6259 |
| I-329 | 2-Br | O | 2-SOMe | mp. [132–136° C.] |
| I-330 | " | " | 2-SO$_2$Me | mp. [148–150° C.] |
| I-331 | " | " | 2-CN | mp. [171–173° C.] |
| I-332 | " | " | 2-OMe | |
| I-333 | " | " | 2,4-Cl$_2$ | mp. [115–116° C.] |
| I-334 | " | " | 3,5-Cl$_2$ | |
| I-335 | " | " | 4-Cl | $N_D^{26.5}$ 1.5883 |
| I-336 | " | " | 3-Cl | $N_D^{26.0}$ 1.6135 |
| I-337 | " | " | 2-I | mp. [97–98° C.] |
| I-338 | " | S | 2-Cl | |
| I-339 | " | " | 2,6-F$_2$ | mp. [136–138° C.] |
| I-340 | 3-Br, 4-OMe | O | " | $N_D^{24.5}$ 1.5690 |
| I-341 | 4-Cl, (2-Me)phenyl | " | " | mp. [90–92° C.] |
| I-342 | 4-Cl, (2-CF$_3$)phenyl | " | " | Vis. oil* |
| I-343 | 4-(2,3-Cl$_2$)phenyl | O | 2,6-F$_2$ | Vis. oil* |
| I-344 | 4-Cl, (2-CF$_3$)phenyl | " | " | Vis. oil* |

TABLE 1-1-continued

| Compound No. | Xn | Z | −Ym | Physical constant |
|---|---|---|---|---|
| I-345 | 4-O-C6H4-CF3 (4-CF3) | " | " | $N_D^{26.0}$ 1.5418 |
| I-346 | 4-O-(2-pyridyl)-CF3 | " | " | $N_D^{31.0}$ 1.5471 |
| I-347 | 4-SO-C6H4-Cl (4-Cl) | " | " | $N_D^{26.0}$ 1.5782 |
| I-348 | 4-O-(4,6-diOMe-pyrimidin-2-yl) | " | " | Vis. oil* |
| I-349 | 4-OCH2C≡CH | " | " | $N_D^{25.0}$ 1.5625 |
| I-350 | 4-SMe | " | " | $N_D^{27.4}$ 1.5782 |
| I-351 | 4-Me | " | " | $N_D^{23.4}$ 1.5423 |
| I-352 | H | " | 4-Cl | $N_D^{27.5}$ 1.5999 |
| I-353 | 2-Cl | O | 4-Cl | $N_D^{27.5}$ 1.5952 |
| I-354** | 2-Br | " | 2-SOMe | mp. [118–121° C.] |
| I-355 | " | " | 4-F | $N_D^{25.3}$ 1.5872 |
| I-356 | " | " | 4-Br | mp. [88–90° C.] |
| I-357 | " | " | 4-Me | $N_D^{27.3}$ 1.5967 |
| I-358 | " | " | 4-$^n$Hep | $N_D^{25.7}$ 1.5789 |
| I-359 | " | " | 4-CF3 | mp. [68–70° C.] |
| I-360 | " | " | 4-OMe | mp. [95–97° C.] |
| I-361 | " | " | 4-SMe | mp. [91–94° C.] |
| I-362 | " | " | 4-NO2 | mp. [140–142° C.] |
| I-363 | " | " | 4-CN | mp. [113–115° C.] |
| I-364 | " | " | 2-F, 4-Cl | $N_D^{26.3}$ 1.6029 |
| I-365 | " | " | 3,4-Cl2 | $N_D^{27.3}$ 1.6102 |
| I-366 | " | " | 2,4,6-Cl3 | $N_D^{27.0}$ 1.6042 |
| I-367 | 4-CH3 | S | 2,6-F2 | mp. [85–87° C.] |
| I-368 | 4-SOMe | O | " | $N_D^{26.5}$ 1.5683 |
| I-369 | 4-SO2Me | " | " | oil* |
| I-370 | 4-(4-$sec$Bu-C6H4) | " | " | $N_D^{24.5}$ 1.5741 |

Mark ** denotes the isomer of I-329.

TABLE 1-2
| Compound No. | R₃ | Z | R₁*¹ | R₂ | —Ym | Physical constant |
|---|---|---|---|---|---|---|
| II-1 | 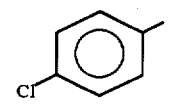 | O | $CH_3$ | $CH_3$ | 2,6-$F_2$ | $N_D^{22.8}$ 1.5367 |
| II-2 | 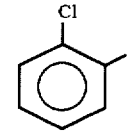 | " | " | " | " | $N_D^{23.9}$ 1.5542 |
| II-3 | " | " | " | " | 2-Cl, 6-F | $N_D^{23.9}$ 1.5270 |
| II-4 | 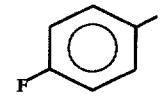 | " | " | " | 2,6-$F_2$ | $N_D^{24.7}$ 1.5502 |
| II-5 | 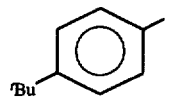 | " | " | " | " | $N_D^{23.9}$ 1.5264 |
| II-6 | 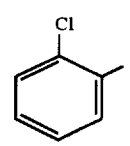 | " | " | " | " | $N_D^{23.8}$ 1.5270 |
| II-7 | " | " | " | " | 2-Cl, 6-F | $N_D^{24.0}$ 1.5420 |
| II-8 | 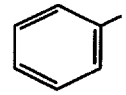 | " | $CH_2CH_3$ (t:c = 1:4) | H | 2,6-$F_2$ | $ND^{23.9}$ 1.5436 |
| II-9 | " | " | $CH_3$ (t:c = 1:4) | " | " | $N_D^{20.7}$ 1.5462 |
| II-10 | 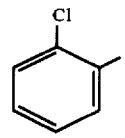 | O | H | $CH_3$ | 2,6-$F_2$ | mp. [78–80° C.] |
| II-11 | 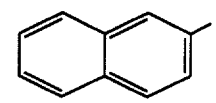 | " | " | " | " | |
| II-12 | 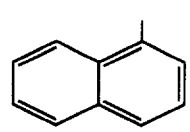 | " | " | H | " | Vis.oil* |
| II-13 |  | " | " | " | " | $N_D^{24.5}$ 1.5951 |

TABLE 1-2-continued

Structure: R3, R2, R1 substituted with A=N-benzene(Ym) group

| Compound No. | R3 | Z | R1*1 | R2 | —Ym | Physical constant |
|---|---|---|---|---|---|---|
| II-14 | phenyl | " | CH3 (t:c = 2:8) | " | " | $N_D^{25.1}$ 1.5398 |
| II-15 | " | " | CH3 (t) | " | " | $N_D^{25.3}$ 1.5485 |
| II-16 | " | " | Et | " | " | |
| II-17 | " | " | iPr | " | " | |
| II-18 | " | " | npen | " | " | |
| II-19 | phenyl | O | phenyl | H | 2,6-F2 | |
| II-20 | 2-Cl-phenyl | " | CH3 (t) | " | " | $N_D^{27.5}$ 1.5465 |
| II-21 | " | " | iPr | " | " | |
| II-22 | " | " | phenyl | " | " | |
| II-23 | 2-Br-phenyl | " | CH3 (c) | " | " | $N_D^{24.5}$ 1.5554 |
| II-24 | " | " | CH3 (t) | " | " | $N_D^{24.5}$ 1.5600 |
| II-25 | " | " | CH3 (t:c = 1:1) | " | " | $N_D^{25.5}$ 1.5595 |
| II-26 | " | " | Et | " | " | |
| II-27 | " | " | iPr (c) | " | " | $N_D^{25.5}$ 1.5477 |
| II-28 | 2-Br-phenyl | O | iPr (t) | H | 2,6-F2 | $N_D^{25.5}$ 1.5489 |
| II-29 | " | " | npen | " | " | |

TABLE 1-2-continued
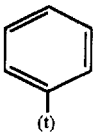
| Compound No. | R₃ | Z | R₁*¹ | R₂ | —Ym | Physical constant |
|---|---|---|---|---|---|---|
| II-30 | " | " | 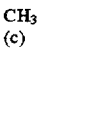 (t) | " | " | mp. [85–86° C.] |
| II-31 | 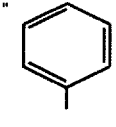 | " | CH₃ (c) | " | " | mp. [159–162° C.] |
| II-32 | " | " | CH₃ (t) | " | " | |
| II-33 | " | " | $^i$Pr | " | " | |
| II-34 | " | " | " 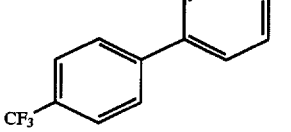 | " | " | |
| II-35 | | " | CH₃ (t) | " | " | mp. [135–136° C.] |
| II-36 | " | " | $^i$Pr | " | " | |
| II-37 | | O | CH₃ (c) | H | 2,6-F₂ | mp. [136–137° C.] |
| II-38 | " | " | $^i$Pr | " | " | |
| II-39 | 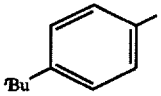 | " | CH₃ (c) | " | " | Vis.oil* |
| II-40 | " | " | $^i$Pr | " | " | |
| II-41 | | " | CH₃ (t:c = 9:1) | " | 2-Cl | $N_D^{27.0}$ 1.5782 |
| II-42 | " | " | Et | " | " | |
| II-43 | " | " | $^i$Pr | " | " | |

TABLE 1-2-continued

| Compound No. | R₃ | Z | R₁*¹ | R₂ | —Ym | Physical constant |
|---|---|---|---|---|---|---|
| II-44 | " | " | Ph | " | " | |
| II-45 | 2-Cl-C₆H₄ | " | $CH_3$ (t:c = 2:1) | " | " | $N_D^{27.0}$ 1.5828 |
| II-46 | 2-Cl-C₆H₄ | O | ⁱPr | H | 2-Cl | |
| II-47 | " | " | Ph | " | " | |
| II-48 | 2-Br-C₆H₄ | " | $CH_3$ (t) | " | " | $N_D^{23.8}$ 1.5944 |
| II-49 | " | " | $CH_3$ (t:c = 3:2) | " | " | $N_D^{25.5}$ 1.5923 |
| II-50 | " | " | ⁱPr | " | " | |
| II-51 | " | " | Ph | " | " | |
| II-52 | 2-Cl-C₆H₄ | " | $CH_3$ (c) | " | 2,6-F₂ | $N_D^{27.5}$ 1.5482 |
| II-53 | " | " | $CH_3$ (c) | " | 4-Cl | $N_D^{26.5}$ 1.5796 |
| II-54 | " | " | $CH_3$ (t) | " | " | $N_D^{26.5}$ 1.5703 |
| II-55 | 2-Br-C₆H₄ | O | $CF_3$ (t) | " | 2,6-F₂ | $N_D^{25.5}$ 1.5270 |

TABLE 1-2-continued

[Structure: R1, R2, R3 substituents on a ring with N, A, connected to phenyl-Ym]

| Compound No. | R3 | Z | R1*1 | R2 | —Ym | Physical constant |
|---|---|---|---|---|---|---|
| II-56 | " | " | phenyl (c) | " | " | mp. [118–120° C.] |
| III-1 | 2-thienyl | O | CH₃ | CH₃ | 2,6-F₂ | $N_D^{24.2}$ 1.5560 |
| III-2 | " | " | H | H | " | $N_D^{23.3}$ 1.5606 |
| III-3 | 5-Br-2-thienyl | " | " | " | " | |
| III-4 | 2-furyl | " | " | " | " | |
| IV-1 | 3-pyridyl | O | H | H | 2,6-F₂ | $N_D^{19.0}$ 1.5558 |
| IV-2 | 6-chloro-3-pyridyl | " | " | " | " | |
| IV-3 | 6-phenoxy-3-pyridyl | " | " | " | " | |
| IV-4 | 5-phenyl-2-pyridyl | " | " | " | " | |
| IV-5 | 6-phenyl-3-pyridyl | " | " | " | " | |
| IV-6 | 6-(4-chlorophenyl)-3-pyridyl | " | " | " | " | |

TABLE 1-2-continued

| Compound No. | R₃ | Z | R₁*¹ | R₂ | —Ym | Physical constant |
|---|---|---|---|---|---|---|
| IV-7 | 2-(4-chlorophenyl)-5-methylpyridin-yl | " | " | " | " | |
| IV-8 | 4-methylpyridin-yl | O | H | H | 2,6-F₂ | $N_D^{19.0}$ 1.5570 |
| IV-9 | 3-chloro-4-methylpyridin-yl | " | " | " | " | |
| IV-10 | 2-chloro-3-methylpyridin-yl | " | " | " | " | |
| IV-11 | 2-methylpyridin-yl | " | " | " | " | |
| IV-12 | 3-chloro-2-methylpyridin-yl | " | " | " | " | |
| IV-13 | 6-methoxy-3-methylpyridin-yl | " | " | " | " | $N_D^{19.0}$ 1.5582 |
| V-1 | H₃C | " | " | " | " | |
| V-2 | ⁱPr | " | " | " | " | |
| V-3 | cyclohexyl-CH | " | " | " | " | $N_D^{23.0}$ 1.5122 |
| V-4 | PhCH₂ | O | H | H | 2,6-F₂ | |
| V-5 | Ph-CH(CH₃) | " | " | " | " | |

TABLE 1-2-continued
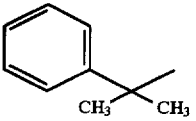
| Compound No. | R₃ | Z | $R_1^{*1}$ | R₂ | —Ym | Physical constant |
|---|---|---|---|---|---|---|
| V-6 | 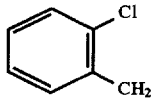 | " | " | " | " | |
| V-7 | 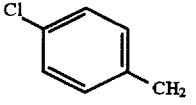 | " | " | " | " | $N_D^{25.0}$ 1.5594 |
| V-8 | CCl₃— | " | " | " | " | |
| V-9 | ⁿC₈H₁₇ | " | " | " | " | |
| V-10 | ⁿC₁₂H₂₅ | " | " | " | " | |
| V-11 | 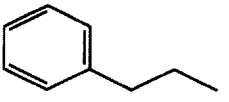 | " | " | " | " | |
| V-12 | 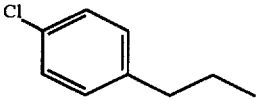 | " | " | " | " | |
| V-13 | 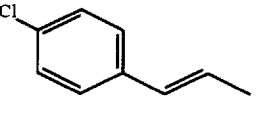 | O | H | H | 2,6-F₂ | |
| V-14 | 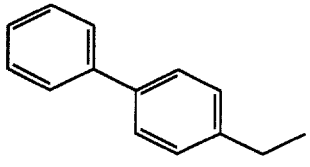 | " | " | " | " | |
| V-15 | 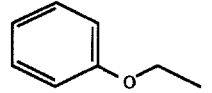 | " | " | " | " | Vis.oil* |
| V-16 | " | " | " | " | 2-Cl, 6-F | Vis.oil* |
| V-17 | 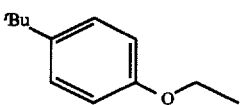 | " | " | " | 2,6-F₂ | $N_D^{23.8}$ 1.5418 |
| V-18 | 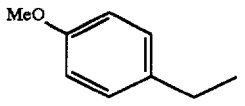 | " | " | " | " | $N_D^{24.5}$ 1.5318 |
| V-19 |  | " | " | " | " | |

TABLE 1-2-continued

| Compound No. | R₃ | Z | $R_1^{*1}$ | R₂ | —Ym | Physical constant |
|---|---|---|---|---|---|---|
| V-20 | 4-Cl-phenyl-O- | " | " | " | " | $N_D^{24.4}$ 1.5445 |
| VI-1 | 2-Br-phenyl-C(CH₃)₂CH₂- | | | | 2,6-F₂-phenyl | $N_D^{27.5}$ 1.5495 |

*¹: t denotes a trans form of R₁ and R₃, and c denotes a cis form of R₁ and R₃.

¹H-NMR Spectrum Data obtained from the Compounds of the Present Invention. [Compound No.] $\delta_{TMS}$ (CDCl₃) (ppm)

[I-40]
1.30(s, 9H), 2.06(m, 1H), 2.37(m, 1H), 4.38(m, 2H), 4.79(m, 1H), 6.93(m, 2H), 7.23–7.46(m, 5H)

[I-70]
1.97(m, 1H), 2.45(m, 1H), 4.38(m, 2H), 4.75(m, 1H), 6.95(m, 2H), 7.22–7.47(m, 3H), 7.65(d, 1H)

[I-86]
1.40(s, 9H), 1.45(t, 3H), 2.02(m, 1H), 2.32(m, 1H), 4.05(q, 2H), 4.35(m,2H), 4.75(m, 1H), 6.82–6.98(m, 3H), 7.08–7.15(m, 1H), 7.23–7.46(m, 5H)

[88]
2.05(m, 1H), 2.40(m, 1H), 4.40(m, 2H), 4.85(q, 1H), 6.93(m, 2H), 7.16(d, 2H), 7.32(m, 1H), 7.45(d, 2H), 7.96(d, 1H), 8.25(d, 1H)

[I-122]
1.85(m, 1H), 2.54(m, 1H), 3.82(s, 3H), 4.41(m, 2H), 5.08(m, 1H), 6.70(m, 1H), 6.95(m, 2H), 7.08(d, 1H), 7.30–7.44(m, 2H)

[I-155]
1.35(s, 9H), 2.08(m, 1H), 2.42(m, 1H), 4.42(m, 2H), 4.90(m, 1H), 6.95(m, 2H), 7.29–7.65(m, 9H)

[I-160]
2.08(m, 1H), 2.38(m, 1H), 4.40(m, 2H), 4.82(m, 1H), 6.94(m, 2H), 7.21–7.54(m, 8H)

[I-165]
1.92(m, 1H), 2.54(m, 1H), 4.42(m, 2H), 5.20(m, 1H), 6.96(m, 2H), 7.28–7.58(m, 8H)

[I-182]
2.00(m, 1H), 2.35(m, 1H), 4.35(m, 2H), 4.80(m, 1H), 6.95(m, 2H), 7.18–7.41(m, 9H)

[I-296]
2.05(m, 1H), 2.40(m, 1H), 4.42(m, 2H), 4.85(m, 1H), 6.92–7.12(m, 6H), 7.30–7.50(m, 3H),8.20(d,2H)

[I-301]
1.48(t, 3H), 2.07(m, 1H), 2.40(m, 1H), 4.12(m, 2H), 4.42(m, 2H), 4.87(m, 1H) 7.05(m, 1H), 7.08–7.57(m, 10H)

[I-304]
1.94(m, 1H), 2.54(m, 1H), 4.44(m, 2H), 5.21(m, 1H), 6.96(m, 2H), 7.27–7.67(m,9H)

[I-305]
1.93(m, 1H), 2.54(m, 1H), 4.43(m, 2H), 5.20(m, 1H), 6.97(m, 2H), 7.28–7.65(m, 8H)

[I-306]
2.08(m, 1H), 2.40(m, 1H), 4.42(m, 2H), 4.83(m, 1H), 6.96(m, 2H), 7.26–7.50(m, 9H)

[I-308]
2.08(m, 1H), 2.42(m, 1H), 4.43(m, 2H), 4.88(m, 1H), 6.95(m, 2H), 7.28–7.75(m, 8H

[I-342]
2.08(m, 1H), 2.42(m, 1H), 4.41(m, 2H), 4.88(m, 1H), 6.93(m, 2H), 7.22–7.56(m, 7H),7.72(d, 1H)

[I-343]
2.03(m, 1H), 2.48(m, 1H), 4.40(m, 2H), 4.82(m, 1H), 6.94(m, 2H), 7.22–7.60(m, 7H),7.68(d, 1H)

[I-344]
2.09(m, 1H), 2.40(m, 1H), 4.42(m, 2H), 4.85(m, 1H), 6.95(m, 2H), 7.23–7.63(m, 8H)

[I-348]
2.02(m, 1H), 2.35(m, 1H), 3.82(s, 6H), 4.40(m, 2H), 4.85(m, 1H), 5.78(s, 1H), 6.94(m, 2H), 7.22(d, 2H), 7.32(m, 1H), 7.40(d, 2H)

[I-369]
2.01(m, 1H), 2.38(m, 1H), 3.05(s, 3H), 4.03(m, 2H), 4.92(m, 1H), 6.95(m, 2H), 7.38(m, 1H), 8.00(m, 4H)

[II-12]
2.11(m, 1H), 2.45(m, 1H), 4.40(m, 2H), 5.00(m, 1H), 6.97((m, 2H), 7.27–7.88(m, 8H)

[II-39]
1.31(s, 9H), 1.37(d, 3H), 2.30(m, 1H),4.57(m, 1H), 4.82 (m, 1H), 6.90(m, 2H), 7.20–7.42(m, 5H)

[V-15]
1.78(m, 1H), 1.97(m, 1H), 2.73(m, 1H), 3.28(m, 1H), 3.85(m, 1H), 4.32(m, 2H), 6.92(m, 2H), 7.22–7.65(m, 10H)

[V-16]
1.80(m, 1H), 1.98(m, 1H), 2.72(m, 1H), 3.30(m, 1H), 3.85(m, 1H), 4.32(m, 2H), 7.02(m, 1H), 7.08–7.63(m, 11H)

The compounds of the present invention can be used for the control of pests against agricultural production, hygienic pest insects, pest insects in storing grains, pest insects of clothing, house pest insects, etc. The representative examples for such pests are exemplified hereinbelow.

For examples of Lepidopterous pest insects, cotton leafworm, cabbage armyworm, black cutworm, common cabbageworm, cabbage looper, diamond-back, smaller tea tortrix, tea leaf roller, peach fruit moth, oriental fruit moth, citrus leaf miner, tea leaf roller, apple leaf miner, gypsy moth, tea tussock moth, rice stem borer, grass leaf roller, European corn borer, fall webworm, almond moth, Heliothis sp., Helicoverpa sp., Agrotis sp., casemaking clothes moth, codling moth, and cotton ballworm are exemplified. For examples of Hemipterous pest insects, green peach aphid, cotton aphid, turnip aphid, grain aphid, bean bug, common green strink bug, arrowhead scale, mulberry mealy scale, greenhouse whitefly, tobacco whitefly, pear psylla, Japanese pear lace bug, brown planthopper, small brown planthopper, white-backed planthopper, and green rice leafhopper are exemplified. For examples of Coleopterous pest insects, striped flea beetle, cucurbit leaf beetle, Colorado potato beetle, rice water weevil, rice weevil, azuki bean weevil, Japanese beetle, soybean beetle, Diabrotica sp., cigarette beetle, powder post beetle, pine sawyer, white-spotted longicorn beetle, Agriotis sp., 28-spotted ladybeetle, rust-red flour beetle, and cotton ball weevil are exemplified. For examples of Dipterous harmful insects, housefly, *Calliphora lata*, *Boettcherisca peregrina*, cucurbit fruit fly, citrus fruit fly, seed maggot, rice leaf miner, yellow drosophila, *Stomoxys calcitrans*, *Culex tritaeniarhynchus*, *Aedes aegypti*, and *Anopheles hyrcanus*, are exemplified. For example of Thysanopterous pest insects, *Thrips palmi*, and tea thrips are exemplified. For examples of Hymenopterus harmful insects, *Monomorium pharaonis*, yellow harnet and cabbage sawfly are exemplified. For examples of Orthopterous harmful insects, German cockroach, American cockroach, Japanese cockroach, and grasshopper are exemplified. Isopterous harmful insects, such as house termite and Japanese white ant, Aphanipterous harmful insects such as human flea, Anoplurous harmful insects such as human louse, mites, such as two-spotted spider mite, carmine mite, Kanzawa spider mite, citrus red mite, European red mite, citrus rust mite, apple rust mite, Tarsonemus sp., Brevipalpus sp., Eotetranychus sp., Robin bulb mite, common grain mite, *Desmatophagoides farinae*, *Boophilus microplus* and *Haemaphysallis bispinosa*, plant-parasitic nematodes, such as southern root-knot nematode, root lesion nematode, soybean cyst namatode, rice white-tip nematode and pine wood nenatode are exemplified.

For the pest insects as exemplified above, the compounds of the present invention has all of excellent adulticidal, nymphcidal, larvicidal and ovicidal activities. Recently, a problem has been raised in the control of the pest insects, such as diamond back, planthoppers, leafhoppers, aphids, and plant mites, since these insects and mites have developed the resistance to insecticides, such as organophosphorus insecticides, carbamate insecticides and acaricides, whereby the activity of those insecticides and acaricides have been decreased. Therefore, a chemical which can be effective against such resistant insects and mites has been desired. The compound of the present invention has an excellent insecticidal and acaricidal activities not only against susceptible strains of those insects and mites but also against the resistant strains of those insect and mite to organophosphorus compounds, carbamate compounds, pyrethroid compounds and acaricides.

Some of the compounds of the present invention have excellent fungicidal activity against wide varieties of phytopathogenic fungi, which can be used for the control of various plant diseases attacking many of agricultural and horticultural crops, flowers, turf and pastures. As the preferable examples of the diseases to be controlled with such compounds, powdery mildew, downy mildew or scab on various crops can be exemplified.

Among the compounds of the present invention, I-43, I-44, I-125, I-335, I-337, I-340, II-10, II-27, V-7, V-17 and VI-3 are particularly effective against the diseases, such as powdery mildew, downy mildew or scab.

The chemical agent for controlling pests specified in the present invention contains a compound represented by the general formula [I] as its active component. The compound can be used for the control agent without formulating, however, it is normally used in a typical applicable form for agricultural chemicals, such as wettable powder, water soluble powder, dust formulation, emulsifiable concentrate, granular formulation, flowable formulation, etc. For additives and carriers when used for solid formulations, plant-origin powder, such as soybean powder and wheat flour, fine mineral powder, such as diatomaceous earth, apatite, gypsum, talc, bentonite and clay, and organic and inorganic materials, such as sodium benzoate, urea and Glauber's salt can be used.

For a solvent to be used in liquid formulations, vegetable oils, mineral oils, distillate fractions of petroleum, such as kerosene, xylene and solvent naphtha, cyclohexane, cyclohexanone, dimethylformamide, dimethylsulfoxide, trichloroethylene, methyl isobutyl ketone, water and the like can be used. In order to obtain homogeneous and stable liquid formulation, a surface active agent may be added to the formulation, if required. The wettable powder, the emulsifiable concentrate, the water soluble powder and the flowable formulation obtained as described above can be used after diluting them, respectively to a desired concentration of the suspension or emulsion. The dust and granular formulations obtained as described above can be used by spray directly to crop plants.

Although the compound of the present invention is sufficiently effective alone, it can also be used in a blend with various kinds of insecticides, acaricides, nematicides, fungicides and synergistic agents.

The representative examples of the insecticides, the acaricides, etc. which can be used for the blend are exemplified in the following.

Organophosphorus and Carbamate Insecticides

Fenthion, fenitrothion, diazinon, chlorpyriphos, ESP, vamidothion, fenthoate, dimethoate, formothion, malathion, trichlorfon, thiometon, phosmet, dichlorvos, acephate, EPBP, methyl parathion, oxydimedon methyl, ethion, salithion, cyanophos, isoxathion, pyridafenthion, phosalon, methydathion, sulprophos, chlorfevinphos, tetrachlorvinphos, dimethylvinphos, propaphos, isofenphos, ethylthiometon, prophenophos, pyracrophos, monocrotophos, azinphos methyl, aldicarb, methomyl, thiodicarb, carbofuran, carbosulfan, benfuracarb, flathiocarb, propoxur, BPMC, MTMC, MIPC, carbaryl, pirimicarb, ethiophencarb, phenoxycarb, cartap, thiocyclam, bensultap, etc.

Pyrethroid insecticides

Permethrin, cypermethrin, deltamethrin, phenvalerate, phenpropathrin, pyrethrin, allethrin, tetramethrin, resmethrin, dimethrin, propathrin, fenothrin, prothrin, fluvalinate, cyfluthrin, cyhalothrin, flucythrinate, ethofenprox, cycloprothrin, tralomethrin, silafluophen, brofenprox, acrinathrin, etc.

Benzoylphenylureas and other insecticides

Diflubenzuron, chlorfluazuron, hexaflumuron, triflumuron, teflubenzuron, flufenoxuron, flucycloxuron, buprofezin, pyriproxyfen, methoprene, benzoepin, diaphenthiuron, imidacloprid, fipronyl, nicotin sulfate, rotenone, meta-aldehyde, machine oil, Bacillus thuringiensis, microbial insecticides such as insect-pathogenic viruses, etc.

Nematocides

Fenamiphos, phosthiazate, etc.

Acaricides

Chlorbenzilate, phenisobromolate, dicofol, amitraz, BPPS, benzomate, hexythiazox, fenbutatin oxide, polynactin, quinomethionate, CPCBS, tetradifon, avermectin, milbemectin, chlofentezin, cyhexatin, pyridaben, fenpyroxymate, tebuphenpyrad, pyrimidifen, fenothiocarb, dienochlor, etc.

Fungicides

Thiophanate methyl, benomyl, carbendazol, thiabendazol, folpet, thiuram, ziram, zineb, manneb, polycarbamate, IBP, EDDP, fthalide, probenazole, isoprothiolane, TPN, captan, polyoxin, blastocidin-S, kasugamycin, streptomycin, validamycin, tricyclazol, pyroquinone, fenazine oxide, mepronyl, flutranyl, pencycron, iprodione, himexazol, metalaxyl, triflumizole, trifolin, triadimefon, bitertanol, fenarimol, propiconazol, simoxanyl, procloraz, peflazoate, hexaconazol, microbutanil, dichlomezine, techlophthalam, propineb, dithianone, fosetyl, vinclozoline, procymidone, oxadixyl, guazatin, propamocarb hydrochloride, fluazinam, oxolinic acid, hydroxyisoxazole, etc.

Now, the examples of the formulations containing the compound of the present invention are described hereinbelow, however, carriers and surfactants to be added thereto shall not be limited to the ones described in the examples.

EXAMPLE 6

Emulsifiable Concentrate

| The inventive compound | 10 parts by weight |
|---|---|
| Alkylphenylpolyoxyethylene | 5 parts by weight |
| Dimethylformamide | 50 parts by weight |
| Xylene | 35 parts by weight |

All components are mixed to dissolve the compound, then to obtain an emulsifiable concentrate, which can be sprayed in a form of emulsion prepared by diluting it with water at use.

EXAMPLE 7

Wettable Powder

| The inventive compound | 10 parts by weight |
|---|---|
| Sulfuric acid ester of higher alcohol | 5 parts by weight |
| Diatomaceous earth | 80 parts by weight |
| Silica | 5 parts by weight |

All components are mixed and micronized to obtain the fine powder, which can be sprayed in a form of suspension by diluting it with water at use.

EXAMPLE 8

Dust Formulation

| The inventive compound | 5 parts by weight |
|---|---|
| Talc | 94.7 parts by weight |
| Silica | 0.3 parts by weight |

All components are mixed and pulverized to obtain dusting powder, which can be sprayed directly at use.

EXAMPLE 9

Granular Formulation

| The inventive compound | 5 parts by weight |
|---|---|
| Clay | 73 parts by weight |
| Bentonite | 20 parts by weight |
| Sodium dioctylsulfosuccinate | 1 part by weight |
| Sodium phosphate | 1 part by weight |

All components are granulated to obtain a granular formulation, which can be applied directly at use.

Industrial Use of the Invention

Test Example 1

Efficacy against cotton aphids

Adults of cotton aphid were inoculated to 10 days old cucumber leaves grown in a 10 cm pot in diameter. The aphids were removed from the leaves 1 day after the inoculation. The emulsifiable concentrate of the inventive compound prepared according to the recipe of the example 6 was diluted with water up to a concentration of 125 ppm normalized to the compound, then the dilution was sprayed to the cucumber leaves where the deposited nymphs of cotton aphid are infesting. The aphids were allowed to stand in a chamber maintained at 25° C. and 65% R.H., then the mortality thereof was checked 6 days later. The result is shown in Table 2.

TABLE 2

| Compound No. | Mortality After 6 Days (%) | Compound No. | Mortality After 6 Days (%) | Compound No. | Mortality After 6 Days (%) | Compound No. | Mortality After 6 Days (%) |
|---|---|---|---|---|---|---|---|
| I-1 | 100 | I-55 | 100 | I-189 | 100 | II-3 | 100 |
| I-2 | 100 | I-56 | 100 | I-193 | 100 | II-4 | 100 |
| I-3 | 100 | I-70 | 100 | I-219 | 100 | II-5 | 100 |
| I-5 | 100 | I-76 | 100 | I-297 | 100 | II-6 | 100 |
| I-6 | 100 | I-79 | 100 | I-298 | 100 | II-7 | 90 |
| I-7 | 100 | I-80 | 100 | I-300 | 89 | II-8 | 100 |
| I-8 | 100 | I-84 | 100 | I-304 | 100 | II-9 | 100 |
| I-9 | 100 | I-86 | 100 | I-305 | 100 | II-10 | 100 |
| I-10 | 100 | I-87 | 100 | I-306 | 100 | II-13 | 100 |
| I-12 | 100 | I-89 | 100 | I-307 | 100 | II-14 | 100 |
| I-13 | 100 | I-90 | 100 | I-312 | 100 | II-15 | 100 |
| I-14 | 100 | I-93 | 100 | I-317 | 100 | II-20 | 100 |
| I-18 | 100 | I-103 | 100 | I-319 | 100 | II-23 | 100 |
| I-19 | 100 | I-105 | 100 | I-322 | 100 | II-24 | 100 |
| I-23 | 100 | I-118 | 100 | I-323 | 100 | II-25 | 100 |
| I-24 | 100 | I-119 | 100 | I-325 | 100 | II-27 | 100 |
| I-25 | 100 | I-120 | 100 | I-326 | 100 | II-28 | 100 |
| I-26 | 100 | I-122 | 100 | I-328 | 100 | II-30 | 100 |
| I-27 | 100 | I-123 | 100 | I-333 | 100 | II-41 | 100 |
| I-28 | 100 | I-124 | 100 | I-337 | 100 | II-45 | 100 |
| I-29 | 100 | I-125 | 100 | I-339 | 100 | II-52 | 100 |
| I-30 | 100 | I-126 | 100 | I-340 | 100 | II-55 | 100 |
| I-31 | 100 | I-127 | 100 | I-341 | 100 | II-56 | 100 |
| I-33 | 100 | I-128 | 100 | I-342 | 100 | III-1 | 100 |
| I-34 | 100 | I-129 | 100 | I-343 | 100 | III-2 | 100 |
| I-35 | 100 | I-145 | 100 | I-344 | 100 | IV-1 | 100 |
| I-36 | 100 | I-149 | 100 | I-345 | 100 | IV-13 | 100 |
| I-37 | 100 | I-150 | 100 | I-346 | 100 | V-3 | 100 |
| I-38 | 100 | I-151 | 100 | I-347 | 100 | V-7 | 100 |
| I-39 | 100 | I-152 | 100 | I-348 | 100 | V-15 | 100 |
| I-40 | 100 | I-153 | 100 | I-349 | 100 | V-16 | 100 |
| I-41 | 100 | I-155 | 100 | I-363 | 100 | V-17 | 100 |
| I-42 | 100 | I-156 | 100 | I-364 | 100 | V-18 | 100 |
| I-43 | 100 | I-160 | 100 | I-366 | 100 | V-20 | 100 |
| I-44 | 100 | I-161 | 100 | II-1 | 100 | VI-1 | 100 |
| I-45 | 100 | I-165 | 100 | II-2 | 100 | | |
| I-46 | 100 | I-169 | 100 | | | | |
| I-51 | 100 | I-180 | 100 | | | Reference Compound A | 6 |
| I-52 | 100 | I-181 | 100 | | | Reference Compound B | 100 |

Reference Compound A

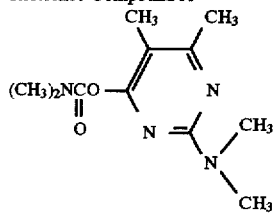

(Pirimicarb)

Reference Compound B

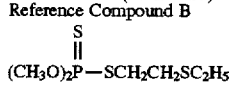

(Thiometon)

Test Example 2

Efficacy against two-spotted spider mites 17 female adults of organophosphorus acaricide-resistant two-spotted spider mites were inoculated on the first true leaf of French bean growing in 6.6 cm pot for 7 to 10 days after germination. Then the suspension of the wettable powder of the inventive compound prepared according to the recipe of the example 4 was adjusted to a concentration of 125 ppm with water to spray for the mites on the leaf. The mites were allowed to stand in a chamber maintained at 25° C. and 65% R.H., then were removed on the third day after spraying. The eggs of the mites depositted during that period were examined on the 11th day after spraying, and the numbers of the mites which could grow up to the adult stage were checked to thereby determine the effectiveness of the inventive compound. The results are shown in Table 3. The effectiveness was calculated according to the following equation.

Acaricidal Efficacy (%) =

$$\frac{\text{No. of Control Adults} - \text{No. of Treated Adults}}{\text{No. of Control Adults}} \times 100$$

TABLE 3

| Compound No. | Acaricidal Efficacy (%) | Compound No. | Acaricidal Efficacy (%) |
|---|---|---|---|
| I-1 | 100 | I-124 | 99 |
| I-2 | 100 | I-125 | 98 |
| I-3 | 100 | I-127 | 95 |
| I-5 | 100 | I-128 | 94 |
| I-7 | 98 | I-149 | 100 |
| I-10 | 99 | I-150 | 99 |
| I-12 | 98 | I-151 | 92 |
| I-13 | 100 | I-153 | 92 |
| I-14 | 100 | I-155 | 100 |
| I-18 | 96 | I-165 | 100 |
| I-23 | 100 | I-180 | 100 |
| I-24 | 99 | I-181 | 100 |
| I-27 | 100 | I-189 | 100 |
| I-30 | 100 | I-297 | 100 |
| I-34 | 100 | I-300 | 100 |
| I-35 | 92 | I-304 | 100 |
| I-37 | 100 | I-305 | 100 |
| I-40 | 100 | I-306 | 97 |
| I-41 | 100 | I-312 | 100 |
| I-43 | 91 | I-319 | 99 |
| I-44 | 99 | I-340 | 92 |
| I-46 | 100 | I-343 | 100 |
| I-51 | 100 | I-345 | 100 |
| I-52 | 100 | I-346 | 99 |
| I-56 | 100 | II-6 | 100 |
| I-70 | 98 | II-31 | 100 |
| I-76 | 100 | II-35 | 100 |
| I-79 | 100 | IV-13 | 92 |
| I-80 | 100 | V-7 | 98 |
| I-89 | 100 | V-15 | 100 |
| I-90 | 100 | V-16 | 98 |
| I-93 | 92 | V-17 | 99 |
| I-118 | 100 | V-18 | 100 |
| I-123 | 99 | V-20 | 99 |
|  |  | Reference Compound C | 55 |

Reference Compound C

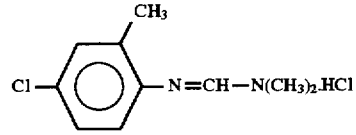

(chlordimeform)

Test Example 3

Efficacy against Armyworm

The suspension of the wettable powder of the inventive compound prepared according to the recipe of the example 4 was adjusted to a concentration of 125 ppm with water. Maize leaves were dipped in the suspension for 30 seconds, dried and put into a petri dish in which 5 third-instar larva of armyworm were placed beforehand. The armyworms in the petri dish was allowed to stand in a chamber maintained at 25° C. and 65% R.H., and the mortality of the armyworm was checked 5 days later. This test was repeated twice. The results are shown in Table 4 hereinbelow.

TABLE 4

| Compound No. | Mortality after 5 days (%) |
|---|---|
| I-89 | 100 |
| I-149 | 100 |
| I-150 | 100 |
| I-151 | 100 |
| I-152 | 100 |
| I-153 | 100 |
| I-155 | 100 |
| I-160 | 100 |
| I-161 | 100 |
| I-165 | 100 |
| I-169 | 100 |
| I-181 | 100 |
| I-189 | 100 |
| I-193 | 100 |
| I-300 | 100 |
| I-301 | 100 |
| I-303 | 100 |
| I-304 | 100 |
| I-305 | 100 |
| I-307 | 100 |
| I-312 | 100 |
| I-322 | 100 |
| I-341 | 100 |
| I-342 | 100 |
| I-343 | 100 |
| II-31 | 100 |
| II-35 | 100 |
| Reference Compound C | 40 |

Test Example 4

Efficacy against Green rice leafhoppers

Young seedlings of rice plant grown for 7 days after germination were dipped for 30 seconds in the emulsion of the emulsifiable concentrate of the inventive compound prepared according to the recipe of the example 3 and adjusted to a concentration of 125 ppm with water. Then the treated seedlings were dried and placed into a test tube. Each 10 third-instar larva of organophosphorus and carbamate insecticides-resistant strain of green rice leafhoppers were then inoculated into the test tube. The test tube was covered with gauze and placed in a chamber maintained at 25° C. and 65% R.H., then the mortality of the leafhoppers was checked on the 5th days after the inoculation. The results are shown in Table 5 hereinbelow.

TABLE 5

| Compound No. | Mortality after 5 days(%) |
|---|---|
| I-56 | 100 |
| I-70 | 100 |
| I-76 | 100 |
| I-307 | 100 |
| I-337 | 80 |
| I-343 | 100 |
| I-344 | 80 |
| II-14 | 100 |
| II-15 | 100 |
| IV-13 | 100 |
| V-3 | 100 |
| V-7 | 100 |
| V-17 | 100 |
| Reference Compound D | 0 |

Reference Compound D

TABLE 5-continued

| Compound No. | Mortality after 5 days(%) |
|---|---|

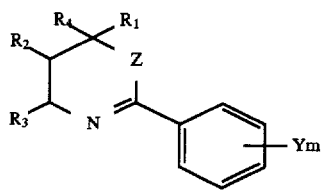

(Malathion)

We claim:

1. A compound represented by the chemical formula [I]:

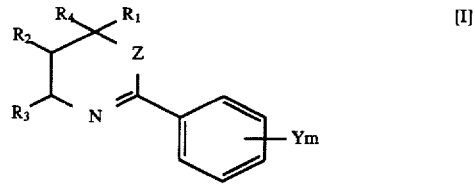

wherein Z is an oxygen atom or a sulfur atom;

Y is a halogen atom; a $(C_1-C_6)$ alkyl group which may be optionally substituted by halogen atom; an optionally substituted $(C_1-C_6)$ alkoxycarbonyl group; $S(O)_p\text{-}r^1$ wherein p denotes an integer of 0 to 2 and $r^1$ represents an optionally substituted $(C_1-c_6)$ alkyl group; nitro; cyano or amino group which may be optionally substituted by mono- or di- $(C_1-C_6)$ alkyl group;

m denotes an integer from 2 to 3;

one Y being at the 2-position of the phenyl ring;

$R_1$, $R_2$ and $R_4$ are the same or different from one another and each independently represent hydrogen, an optionally substituted $(C_1-C_6)$ alkyl group or an optionally substituted phenyl group. $R_3$ represents a $(C_1-C_{18})$ alkyl group, a $(C_1-C_6)$ alkenyl group, an aralkyl, a $(C_3-C_8)$ cycloalkyl group, phenyl, naphthyl, pyridyl, furyl or thienyl, which may be substituted by halogen atom; hydroxy group; a $(C_1-C_{18})$ alkyl group; a $(C_1-C_6)$ alkyl group which may be optionally substituted by halogen atom, phenyl group, a halophenyl group or a $(C_1-C_6)$ alkoxyphenyl group; an optionally substituted $(C_3-C_8)$ cycloalkyl group; phenyl group which may be optionally substituted by halogen atom, a $(C_1-C_{18})$ alkyl group, a $(C_1-C_6)$ haloalkyl group, a $(C_1-C_6)$ alkoxy group or a $(C_1-C_6)$ haloalkoxy group; a $(C_1-C_{18})$ alkoxy group; a $(C_1-C_8)$ haloalkoxy group, a phenyl-$(C_1-C_6)$ alkoxy group which may be substituted by halogen atom, a $(C_1-C_6)$ alkyl group, a $(C_1-C_6)$ haloalkyl group, a $(C_1-C_6)$ alkoxy group or a $(C_1-C_6)$ haloalkoxy group; a pyridyl-$(C_1-C_6)$ alkoxy group which may be substituted by halogen atom; an optionally substituted $(C_2-C_6)$ alkynyloxy group; a phenoxy group which may be substituted by halogen, a $(C_1-C_6)$ alkoxy group or nitro; pyridyl which may be substituted by halogen atom or a $(C_1-C_6)$ alkyl; a heterocyclic-oxy group which may be substituted by halogen atom, a $(C_1-C_6)$ alkyl group, a $(C_1-C_6)$ haloalkyl group or a $(C_1-C_6)$ alkoxy group; $S(O)_q\text{-}r^2$ wherein q denotes an integer of 0, 1 or 2, $r^2$ represents an optionally substituted $(C_1-C_6)$ alkyl group or phenyl which may be substituted by halogen; amino group which may be substituted by mono- or di-$(C_1-C_6)$ alkyl group, provided that if Z is a sulfur atom, Y is not a $(C_1-C_6)$ alkyl group.

2. A pesticidal composition of matter comprising a pesticidally effective amount of a compound represented by the chemical formula [I]: wherein Z is an oxygen atom or a sulfur atom;

[I]

Y is a halogen atom; a $(C_1-C_6)$ alkyl group which may be optionally substituted by halogen atom; an optionally substituted $(C_1-C_6)$ alkoxycarbonyl group; $S(O)_p\text{-}r^1$ wherein p denotes an integer of 0 to 2 and $r^1$ represents an optionally substituted $(C_1-c_6)$ alkyl group; nitro; cyano or amino group which may be optionally substituted by mono- or di- $(C_1-C_6)$ alkyl group;

m denotes an integer from 1 to 3;

$R_1$, $R_2$ and $R_4$ are the same or different from one another and each independently represent hydrogen, an optionally substituted $(C_1-C_6)$ alkyl group or an optionally substituted phenyl group.

$R_3$ represents a $(C_1-C_{18})$ alkyl group, a $(C_1-C_6)$ alkenyl group, an aralkyl, a $(C_3-C_8)$ cycloalkyl group, phenyl, naphthyl, pyridyl, furyl or thienyl, which may be substituted by halogen atom; hydroxy group; a $(C_1-C_{18})$ alkyl group; a $(C_1-C_6)$ alkyl group which may be optionally substituted by halogen atom, phenyl group, a halophenyl group or a $(C_1-C_6)$ alkoxyphenyl group; an optionally substituted $(C_3-C_8)$ cycloalkyl group; phenyl group which may be optionally substituted by halogen atom, a $(C_1-C_{18})$ alkyl group, a $(C_1-C_6)$ haloalkyl group, a $(C_1-C_6)$ alkoxy group or a $(C_1-C_6)$ haloalkoxy group; a $(C_1-C_{18})$ alkoxy group; a $(C_1-C_8)$ haloalkoxy group, a phenyl-$(C_1-C_6)$ alkoxy group which maybe substituted by halogen atom, a $(C_1-C_6)$ alkyl group, a $(C_1-C_6)$ haloalkyl group, a $(C_1-C_6)$ alkoxy group or a $(C_1-C_6)$ haloalkoxy group; a pyridyl-$(C_1-C_6)$ alkoxy group which may be substituted by halogen atom; an optionally substituted $(C_2-C_6)$ alkynyloxy group; a phenoxy group which may be substituted by halogen, a $(C_1-C_6)$ alkoxy group or nitro; pyridyl which may be substituted by halogen atom or a $(C_1-C_6)$ alkyl; a heterocyclic-oxy group which may be substituted by halogen atom, a $(C_1-C_6)$ alkyl group, a $(C_1-C_6)$ haloalkyl group or a $(C_1-C_6)$ alkoxy group; $S(O)_q\text{-}r^2$ wherein q denotes an integer of 0, 1 or 2, $r^2$ represents an optionally substituted $(C_1-C_6)$ alkyl group or phenyl which may be substituted by halogen; amino group which may be substituted by mono- or di-$(C_1-C_6)$ alkyl group, in admixture with a pesticidally acceptable carrier.

\* \* \* \* \*